United States Patent
An et al.

(10) Patent No.: US 8,785,442 B2
(45) Date of Patent: Jul. 22, 2014

(54) COMPOUND AS ANTAGONIST OF LYSOPHOSPHATIDIC ACID RECEPTOR, COMPOSITION, AND USE THEREOF

(75) Inventors: Songzhu An, Guangzhou (CN); Chufang Li, Guangzhou (CN); Guisheng Zhou, Guangzhou (CN); Chen Huang, Guangzhou (CN)

(73) Assignee: Curegenix, Inc., Guangzhou (CN)

( * ) Notice: Subject to any disclaimer, the term of this patent is extended or adjusted under 35 U.S.C. 154(b) by 0 days.

(21) Appl. No.: 13/982,456

(22) PCT Filed: Jan. 30, 2011

(86) PCT No.: PCT/CN2011/070819
§ 371 (c)(1),
(2), (4) Date: Sep. 25, 2013

(87) PCT Pub. No.: WO2012/100436
PCT Pub. Date: Aug. 2, 2012

(65) Prior Publication Data
US 2014/0031353 A1    Jan. 30, 2014

(51) Int. Cl.
*C07D 417/12* (2006.01)
*C07D 401/12* (2006.01)
*C07D 295/26* (2006.01)
*C07D 261/16* (2006.01)
*C07D 413/04* (2006.01)
*C07D 261/14* (2006.01)

(52) U.S. Cl.
CPC ............. *C07D 417/12* (2013.01); *C07D 261/14* (2013.01); *C07D 413/04* (2013.01); *C07D 401/12* (2013.01); *C07D 261/16* (2013.01); *C07D 295/26* (2013.01)
USPC ........ 514/236.8; 514/365; 514/326; 514/340; 548/245; 548/200; 546/209; 546/272.1

(58) Field of Classification Search
USPC ....................... 514/236.8, 380, 365, 326, 340; 546/209, 272.1; 548/245, 200
See application file for complete search history.

(56) References Cited

U.S. PATENT DOCUMENTS

2010/0152257 A1    6/2010    Hutchinson et al.
2011/0082164 A1    4/2011    Clark et al.

OTHER PUBLICATIONS

International Search Report on PCT/CN2011/070819 dated Nov. 17, 2011.

*Primary Examiner* — San-Ming Hui
*Assistant Examiner* — Kathrien Cruz
(74) *Attorney, Agent, or Firm* — K&L Gates LLP; Louis C. Cullman

(57) ABSTRACT

The present invention relates to a compound as antagonist of LPA receptor, and a pharmaceutical composition comprising the same. The present invention also relates to the use of the compound and the composition, and a method of using the compound to treat, prevent or diagnose diseases, disorders or conditions associated with one or more of the LPA receptors.

9 Claims, No Drawings

COMPOUND AS ANTAGONIST OF LYSOPHOSPHATIDIC ACID RECEPTOR, COMPOSITION, AND USE THEREOF

CROSS REFERENCE TO RELATED APPLICATION

This application is a national phase application of International Patent Application No. PCT/CN2011/070819 filed on Jan. 30, 2011, the entire contents of which are incorporated by reference herein.

FIELD OF THE INVENTION

The present invention relates to a compound as antagonist of lysophatidic acid (LPA) receptor, as well as pharmaceutical composition comprising the same. The present invention also relates to the use of the compound and the composition and a method of using the compound to treat, prevent or diagnose diseases, disorders or conditions associated with one or more of the LPA receptors.

BACKGROUND OF THE INVENTION

Lysophosphatidic acid (1-acyl-2-hydroxy-sn-glycero-3-phosphate; LPA) is a bioactive lipid mediator derived from membrane lipids through the actions of several enzymatic reactions involving phospholipase A2 and lysophospholipase D, lysoPLD/autotaxin (Moolenaar, 2007; Nakanaga, 2010). LPA plays a role in several cellular functions such as proliferation, differentiation, survival, migration and invasion. These functions influence many physiological and pathological processes including angiogenesis, wound repair, fibrosis, inflammation and carcinogenesis. Small molecule compounds that antagonize LPA receptors can be used in the treatment of diseases, disorders or conditions that are dependent on or mediated by LPA (Tigyi, 2010).

LPA acts on G protein-coupled receptors (GPCRs) on target cells. LPA binding to specific GPCRs of 6 subtypes (LPA1, LPA2, LPA3, LPA4, LPA5, LPA6) activates intracellular signaling pathways to produce a series of biological responses (Chun, 2010). LPA1 (EDG2) is expressed in many tissues in adult humans (An, 1997). LPA2 (EDG-4) is expressed in the human testis, pancreas, prostate, thymus, spleen, and peripheral blood leukocytes and in various cancer cell lines (An, 1998). LPA3 (EDG-7) is expressed in human heart, pancreas, prostate, testis, lung, ovary, and brain (Bandoh, 1999). LPA4 (p2y9/GPR23), LPA5 (GPR92) and LPA6 (p2y5) are members of the purinoceptor cluster of GPCRs and are more remotely related to LPA1, LPA2 and LPA3 (Tigyi, 2010).

LPA has long been known as a mitogen for fibroblasts (van Corven, 1989) and as a factor that stimulates production of connective tissue growth factor (CTGF) which promotes fibrosis (Hahn, 2000; Jeon, 2008). LPA also induces expression and activation of a chloride channel that is required for fibroblast-to-myofibroblast differentiation during wound healing (Yin, 2008). More recent studies showed that LPA plays a role in kidney (Pradere, 2007), liver (Watanabe, 2007), eye (Yin, 2008) and lung fibrosis (Tager, 2008). In animal models, LPA1 gene deletion and pharmacological inhibition of the $LPA_1$ receptor suppressed the progression of fibrosis (Pradere, 2007; Tager, 2008; Swaney, 2010). Thus, LPA1 receptor antagonist may become novel therapies for the treatment of fibrosis.

Also, LPA and its GPCRs may play a role in the development of several types of cancers (Mills and Moolenaar, 2007). LPA is a mitogen that increases proliferation of many cell types, including tumor cells (Yang, 2005). LPA may also contribute to tumor progression by increasing motility and invasiveness of cells. Autotaxin (ATX) is a pro-metastatic enzyme initially isolated from the conditioned medium of human melanoma cells that stimulates a number of biological activities, including angiogenesis and the promotion of cell growth, migration, survival, and differentiation through the production of LPA. LPA receptor antagonist Ki16425 blocked the LPA-induced and ascites-induced invasion activity of a highly peritoneal metastatic pancreatic cancer cell line (Yamada, 2004). Ki16425 also inhibited metastasis of breast cancer cells to bone in animal models (Boucharaba, 2006). Therefore, genetic or pharmacological inhibition of LPA receptor signaling represents new approaches for cancer therapies.

Otherwise, after LPA is released at the site of tissue injury, LPA1 plays an important role in the initiation of neuropathic pain (Inoue, 2004).

SUMMARY OF THE INVENTION

The present invention provides a compound as antagonist of LPA, pharmaceutically acceptable salts, prodrugs, and solvates thereof, and the use of such compound. Also, the present provides a method to treat patients suffering from one or more LPA-dependent or LPA-mediated conditions or diseases.

DEFINITIONS

The term "fibrosis" as used herein refers to conditions that are associated with the abnormal accumulation of collagen and fibroblasts. The term includes but are not limited to fibrosis of individual organs or tissues such as the lung, kidney, liver, gastrointestinal (GI) tract, skin, eye, and muscle. Examples include but are not limited to: lung fibrosis: idiopathic pulmonary fibrosis, lung fibrosis caused by radiation or drug, acute or chronic lung injury and acute respiratory distress that are caused by bacterial pneumonia, viral pneumonia, trauma, ventilator, non-pulmonary sepsis; kidney fibrosis: fibrosis after glomerulonephritis caused by systemic inflammatory diseases such as lupus and scleroderma, diabetes, glomerular nephritis, focal segmental glomerular sclerosis, IgA nephropathy, hypertension, and allograft; liver fibrosis: cirrhosis, alcohol induced liver fibrosis, nonalcoholic steatohepatitis (NASH), biliary duct injury, primary biliary cirrhosis, infection or viral induced liver fibrosis (e.g., chronic HBV or HCV infection), and autoimmune hepatitis; GI track fibrosis: scleroderma, and radiation induced GI track fibrosis; head and neck fibrosis, e.g., radiation induced; corneal scarring, e.g., LASIK (laser-assisted in situ keratomileusis) surgery, corneal transplant, and trabeculectomy; skin fibrosis: atopic dermatitis, bullous disorders, psoriatic lesions, dermatitis, contact dermatitis, eczema, rosacea, abnormal wound healing, scarring; and other fibrotic diseases: scleroderma, spinal cord injury induced fibrosis, myelofibrosis, atherosclerosis, vascular restenosis, sarcoidosis, and other connective tissue diseases.

The term "cancer" as used herein refers to an abnormal growth of cells that proliferate in an uncontrolled way and, in some cases, to invade to adjacent tissues, or to metastasize to distant organs. The types of cancer include, but are not limited to, solid tumors (such as those of the brain, breast, bladder, colorectal, endometrium, kidney, lung, lymphatic tissue, ovary, pancreas, thyroid, prostate, skin or blood at any stage with or without metastases.

DESCRIPTION OF THE INVENTION

In one aspect, the present invention provides a compound that blocks the binding of LPA to its receptors, and inhibits LPA-elicited biological responses; therefore, the compound may be useful as antagonist of LPA receptor and as agent for the treatment or prevention of diseases in which inhibition of LPA bioactivity is desired, wherein the compound has the structure of Formula (I):

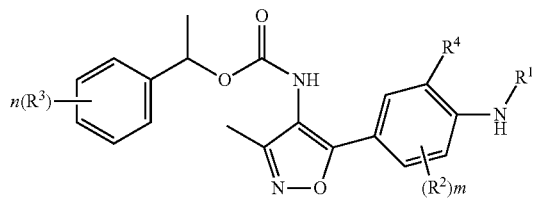

(I)

or a pharmaceutically acceptable salt, solvate, or prodrug thereof, wherein,
when $R^4$ is H, $R^1$ is C(=O)$R^5$ or $SO_2R^5$; or
$R^4$ and $NHR^1$, together with the two C atoms of the phenyl ring to which $R^4$ and $NHR^1$ are respectively attached, form a fused saturated, partially saturated or unsaturated 5-7 membered heterocycle which optionally contains 1-2 heteroatoms selected from N, O or S in addition to the N atom shown;
each $R^2$ and $R^3$ is independently selected from H, F, Cl, Br, CN, OH, or C1-$C_4$alkyl;
$R^5$ is $C_1$-$C_6$ alkyl, $C_1$-$C_6$ aryl, $C_1$-$C_6$ alkoxyl, $C_{3-6}$ cycloalkyl, 5 or 6 membered heteroaryl containing 1-2 heteroatoms selected from N, O or S; 5-6 membered heterocyclyl containing 1-2 heteroatoms selected from N, O or S, wherein $C_1$-$C_6$ alkyl, $C_1$-$C_6$ aryl, $C_1$-$C_6$ alkoxyl, $C_{3-6}$ cycloalkyl, 5 or 6 membered heteroaryl and 5-6 membered heterocyclyl are optionally substituted with F, Cl, Br, I, —CN, —C(=O)—OH, —C(=O)—O—$C_{1-6}$ alkyl, —S(=O)$_2$—$C_{1-6}$ alkyl;
each m and n is 0, 1 or 2.

In another embodiment, the compound is racemic but prefers an isomer as below formula (II):

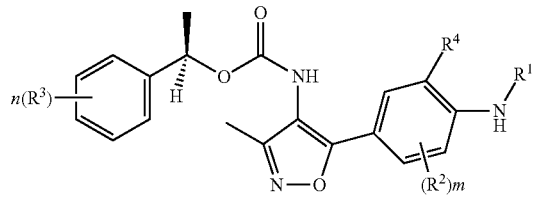

(II)

As used herein, an H atom in any substituent group (e.g., $CH_2$) encompasses all suitable isotopic variations, e.g., H, $^2$H and $^3$H.

As used herein, other atoms in any substituent groups encompasses all suitable isotopic variations, including but are not limited to $^{11}$C, $^{13}$C, $^{14}$C, $^{15}$N, $^{17}$O, $^{18}$O, $^{35}$S, $^{18}$F, $^{36}$I and/or $^{123}$I.

In a preferred embodiment, the example of the compound of the invention includes but is not limited to:
1-(2-chlorophenyl)ethyl(5-(1H-indol-5-yl)-3-methylisoxazol-4-yl)carbamate;
1-(2-chlorophenyl)ethyl(5-(1H-indazol-5-yl)-3-methylisoxazol-4-yl)carbamate;
1-(2-chlorophenyl)ethyl(5-(4-acetamidophenyl)-3-methylisoxazol-4-yl)carbamate;
1-(2-chlorophenyl)ethyl(3-methyl-5-(4-propionamidophenyl)isoxazol-4-yl)carbamate;
1-(2-chlorophenyl)ethyl(5-(4-isobutyramidophenyl)-3-methylisoxazol-4-yl)carbamate;
1-(2-chlorophenyl)ethyl(5-(4-(cyclopropanecarboxamido)phenyl)-3-methylisoxazol-4-yl)carbamate;
1-(2-chlorophenyl)ethyl(3-methyl-5-(methyl(4-methylisoxazol-3-yl)phenyl)carbamate)carbamate;
methyl 3-((4-(4-(((1-(2-chlorophenyl)ethoxy)carbonyl)amino)-3-methylisoxazol-5-yl)phenyl)amino)-3-oxopropanoate;
methyl 1-((4-(4-(((1-(2-chlorophenyl)ethoxy)carbonyl)amino)-3-methylisoxazol-5-yl)phenyl)carbamoyl)cyclopropanecarboxylate;
1-((4-(4-(((1-(2-chlorophenyl)ethoxy)carbonyl)amino)-3-methylisoxazol-5-yl)phenyl)carbamoyl)cyclopropanecarboxylic acid;
4-((4-(4-(((1-(2-chlorophenyl)ethoxy)carbonyl)amino)-3-methylisoxazol-5-yl)phenyl)amino)-4-oxobutanoic acid;
1-(2-chlorophenyl)ethyl(3-methyl-5-(4-(2-(methylsulfonyl)acetamido)phenyl)isoxazol-4-yl)carbamate;
1-(2-chlorophenyl)ethyl(5-(4-(2-cyanoacetamido)phenyl)-3-methylisoxazol-4-yl)carbamate;
1-(2-chlorophenyl)ethyl(5-(4-(2-ethoxyacetamido)phenyl)-3-methylisoxazol-4-yl)carbamate;
1-(2-chlorophenyl)ethyl(5-(4-benzamidophenyl)-3-methylisoxazol-4-yl)carbamate;
1-(2-chlorophenyl)ethyl(3-methyl-5-(4-(thiazole-2-carboxamido)phenyl)isoxazol-4-yl)carbamate;
4-((4-(4-(((1-(2-chlorophenyl)ethoxy)carbonyl)amino)-3-methylisoxazol-5-yl)phenyl)carbamoyl)benzoic acid;
(R)-1-(2-chlorophenyl)ethyl(3-methyl-5-(4-(methylsulfonamido)phenyl)isoxazol-4-yl)carbamate;
1-(2-chlorophenyl)ethyl(5-(4-(ethylsulfonamido)phenyl)-3-methylisoxazol-4-yl)carbamate;
1-(2-chlorophenyl)ethyl(3-methyl-5-(4-(1-methylethylsulfonamido)phenyl)isoxazol-4-yl)carbamate;
1-(2-chlorophenyl)ethyl(5-(4-(cyclopropanesulfonamido)phenyl)-3-methylisoxazol-4-yl)carbamate;
1-(2-chlorophenyl)ethyl(5-(4-(cyclohexanesulfonamido)phenyl)-3-methylisoxazol-4-yl)carbamate;
1-(2-chlorophenyl)ethyl(3-methyl-5-(4-(2,2,2-trifluoroethylsulfonamido)phenyl)isoxazol-4-yl)carbamate;
1-(2-chlorophenyl)ethyl(3-methyl-5-(4-(morpholine-4-sulfonamido)phenyl)isoxazol-4-yl)carbamate;
1-(2-chlorophenyl)ethyl(5-(4-(1-ethylpiperidine-4-sulfonamido)phenyl)-3-methylisoxazol-4-yl)carbamate;
methyl 3-(N-(4-(4-(((1-(2-chlorophenyl)ethoxy)carbonyl)amino)-3-methylisoxazol-5-yl)phenyl)sulfamoyl)propanoate;
3-(N-(4-(4-(((1-(2-chlorophenyl)ethoxy)carbonyl)amino)-3-methylisoxazol-5-yl)phenyl)sulfamoyl)propanoic acid;
1-(2-chlorophenyl)ethyl(3-methyl-5-(4-(phenylsulfonamido)phenyl)isoxazol-4-yl)carbamate;
1-(2-chlorophenyl)ethyl(3-methyl-5-(4-(pyridine-3-sulfonamido)phenyl)isoxazol-4-yl)carbamate;
1-(2-chlorophenyl)ethyl(5-(3-fluoro-4-(methylsulfonamido)phenyl)-3-methylisoxazol-4-yl)carbamate;
1-(2-chlorophenyl)ethyl(5-(2-fluoro-4-(methylsulfonamido)phenyl)-3-methylisoxazol-4-yl)carbamate;
1-(2-chlorophenyl)ethyl(5-(3,5-difluoro-4-(methylsulfonamido)phenyl)-3-methylisoxazol-4-yl)carbamate;

1-(2-chlorophenyl)ethyl(5-(3-chloro-4-(methylsulfona-mido)phenyl)-3-methylisoxazol-4-yl)carbamate;
1-(2-chlorophenyl)ethyl(5-(2-chloro-4-(methylsulfona-mido)phenyl)-3-methylisoxazol-4-yl)carbamate;
1-(2-chlorophenyl)ethyl(3-methyl-5-(3-methyl-4-(methyl-sulfonamido)phenyl)isoxazol-4-yl)carbamate;
1-(3-chlorophenyl)ethyl(3-methyl-5-(4-(methylsulfona-mido)phenyl)isoxazol-4-yl)carbamate;
1-(3-fluorophenyl)ethyl(3-methyl-5-(4-(methylsulfona-mido)phenyl)isoxazol-4-yl)carbamate;
1-(3,4-difluorophenyl)ethyl(3-methyl-5-(4-(methylsulfona-mido)phenyl)isoxazol-4-yl)carbamate;
1-(3,4-dichlorophenyl)ethyl(3-methyl-5-(4-(methylsulfona-mido)phenyl)isoxazol-4-yl)carbamate;
1-(4-chlorophenyl)ethyl(3-methyl-5-(4-(methylsulfona-mido)phenyl)isoxazol-4-yl)carbamate;
1-(2-chloro-4-fluorophenyl)ethyl(3-methyl-5-(4-(methyl-sulfonamido)phenyl)isoxazol-4-yl)carbamate;
1-(2,4-dichlorophenyl)ethyl(3-methyl-5-(4-(methylsulfona-mido)phenyl)isoxazol-4-yl)carbamate;
1-(4-chloro-2-fluorophenyl)ethyl(3-methyl-5-(4-(methyl-sulfonamido)phenyl)isoxazol-4-yl)carbamate;
(R)-1-(2-chloro-4-fluorophenyl)ethyl(3-methyl-5-(4-(meth-ylsulfonamido)phenyl)isoxazol-4-yl)carbamate;
(R)-1-(2-chloro-4-fluorophenyl)ethyl(3-methyl-5-(4-(meth-ylsulfonamido)phenyl)isoxazol-4-yl)carbamate;
(R)-1-(2-chlorophenyl)ethyl(5-(2-fluoro-4-(methylsulfona-mido)phenyl)-3-methylisoxazol-4-yl)carbamate;
(R)-3-(N-(4-(4-(((1-(2-chlorophenyl)ethoxy)carbonyl) amino)-3-methylisoxazol-5-yl)phenyl)sulfamoyl)pro-panoic acid;
(R)-3-(N-(4-(4-(((1-(2-chlorophenyl)ethoxy)carbonyl) amino)-3-methylisoxazol-5-yl)-3-fluorophenyl)sulfa-moyl)propanoic acid;
(R)-4-((4-(4-(((1-(2-chlorophenyl)ethoxy)carbonyl)amino)-3-methylisoxazol-5-yl)phenyl)amino)-4-oxobutanoic acid; or
(R)-4-((4-(4-(((1-(2-chlorophenyl)ethoxy)carbonyl)amino)-3-methylisoxazol-5-yl)-3-fluorophenyl)amino)-4-oxobu-tanoic acid.

In another aspect, the present invention provides a pharmaceutical composition comprising a therapeutically effective amount of the present compound or the pharmaceutically acceptable salt thereof and at least one pharmaceutically acceptable inactive ingredient, such as carrier or diluent. Such composition may be manufactured in a conventional manner by mixing, granulating or coating method for intravenous injection, oral administration, inhalation, nasal administration, subcutaneous injection, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

Preferably, the present composition may be an oral composition, injectable composition or suppository.

In one embodiment of the invention, the composition is an oral composition and may be a tablet or gelatin capsule comprising the present compound as active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets, together with c) binders, e.g., magnesium aluminum silicate, starch paste, gelatin, tragam-ayth, methylcellulose, sodium carboxymethylcellulose and/ or polyvinylpyrrolidone; and if desired, d) disintegrants, e.g., starches, agar, alginic acid or its sodium salt, or effervescent mixtures; and/or e) absorbents, colorants, flavors and sweeteners.

In another embodiment, the composition is an injectable composition and may be an aqueous isotonic solution or suspension.

In yet another embodiment, the composition is suppository and may be prepared from fatty emulsion or suspension.

Preferably, the composition is sterilized and/or contains adjuvant. Such adjuvant can be preserving, stabilizing, wetting or emulsifying agent, solution promoter, salt for regulating the osmotic pressure, buffer and/or any combination thereof.

Alternatively or in addition, the composition may further contain other therapeutically valuable substances for different applications, like solubilizers, stabilizers, tonicity enhancing agents, buffers and/or preservatives.

In an embodiment of the invention, the composition may be a formulation suitable for transdermal application. Such formulation includes an effective amount of the compound of the present invention and a carrier. Preferably, the carrier may include absorbable pharmacologically acceptable solvents to assist passage through the skin of the host. A transdermal device contain the formulation may also be used. The transdermal device may be in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Otherwise, a matrix transdermal formulation may also be used.

In another embodiment of the invention, the composition may be a formulation suitable for topical application, such as to the skin and eyes, and may be aqueous solution, ointment, cream or gel well known in the art.

In another aspect, the present invention provides the use of the compound, as well as the pharmaceutically acceptable salt, solvate, and prodrug thereof, as an antagonist of at least one subtype of the LPA receptors selected from LPA1, LPA2, LPA3, LPA4, LPA5 and LPA6. In one embodiment, the present compound is antagonist of LPA1 receptor. In some embodiments, the present compound is selective antagonist for the LPA1 receptor.

For medical use, the present compound is useful for the treatment or prevention of organ fibrosis (including but not limited to lung fibrosis, liver fibrosis, cirrhosis, renal fibrosis, heart fibrosis, idiopathic pulmonary fibrosis, scleroderma, radiation-induced fibrosis, and drug-induced fibrosis), proliferative disease (including but not limited to tumors, tumor invasion, tumor metastasis), inflammatory diseases (including but not limited to psoriasis and pneumonitis), renal diseases (including but not limited to nephrotitis), urinogenital diseases (including but not limited to benign prostatic hyperplasia), angiogenic disorders (including but not limited to macular degeneration, blood vessel obstruction), neural disease (including but not limited to cerebral infarction and hemorrhage), neuropathic pain, radiation-induced tissue damages (including but not limited to radiation-induced lung pneumonitis and fibrosis) and drug-induced tissue damages (including but not limited to drug-induced lung fibrosis, drug-induced pneumonitis, drug-induced liver fibrosis, drug-induced acute interstitial nephritis).

In one particular embodiment, the present compound is used in the treatment of symptomology or progression of fibrotic diseases or conditions, including but not limited to fibrosis arising from genetic, epigenic, immunological, infectious, metabolic, oncological, toxic, surgical, idiopathic, radiation, drug, and/or traumatic etiology.

In another embodiment, the present compound is used in the treatment of cancer. Preferably, the compound is used in the treatment of malignant and benign proliferative disease. More preferably, the compound is used to prevent or reduce proliferation of tumor cells, invasion and metastasis of tumors.

In yet another embodiment, the present compound is used in the treatment of pain in a human subject. Preferably, the pain is acute pain or chronic pain. More preferably, the pain is neuropathic pain or cancer pain.

In yet another aspect, the present invention provides the use of the compound in the preparation of medicaments for the treatment of LPA-dependent or LPA-mediated diseases or condition.

In yet another aspect, the present invention provides a method of treating or preventing the disease or condition relating to LPA, involving administration of pharmaceutical compositions that include the present compound or pharmaceutically acceptable salt, pharmaceutically active metabolite, prodrug, or solvate thereof, in a therapeutically effective amount to said subject.

In one embodiment is a method for preventing a fibrosis condition in a human subject, the method comprising administering to the human subject at risk of developing one or more fibrosis conditions a therapeutically effective amount of the present compound. In one aspect of this embodiment, the human subject has been exposed to one or more environmental conditions that are known to increase the risk of fibrosis of an organ or tissue. In one aspect, the human subject has been exposed to one or more environmental conditions that are known to increase the risk of fibrosis. In one aspect, the human subject has a genetic predisposition of developing fibrosis of an organ or tissue. In one aspect, the present compound is administered to a human subject to prevent or minimize scarring following injury. In one aspect, injury includes surgery. In another aspect, injury includes radiation therapy. In yet another aspect, injury includes drug-induced.

In another embodiment, the invention provides a method of treating fibrosis comprising administering to the human subject a therapeutically effective amount of the present compound.

In yet another embodiment, the present invention provides a method of treating cancer in a human subject, the method comprising administering to the human subject a therapeutically effective amount of the present compound and/or a second therapeutic agent, wherein the second therapeutic agent is an anti-cancer agent.

In yet another embodiment, the present invention provides a method of treating pain in a human subject, the method comprising administering to the human subject a therapeutically effective amount of the present compound.

The compound of the invention will be administered in therapeutically effective amounts via any of the usual and acceptable modes known in the art, either singly or in combination with one or more therapeutic agents, when synergistic effect may occur. Where the compound of the invention is administered in conjunction with other therapies, dosages of the co-administered compounds will of course vary depending on the type of co-drug employed, on the specific drug employed, on the condition being treated and so forth.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

If the patient's condition does improve, the dose of administered drug may be reduced or suspended for a certain length of time. The length of time may be 2 days to 1 year. In one embodiment, the length of time is 2 days to a week, including 3 days, 4 days, 5 days, and 6 days. In another embodiment, the length of time is within two weeks, such as 10 days and 12 days. In another embodiment, the length of time is within four weeks, such as 15 days and 20 days. In another embodiment, the patient's condition improves obviously, and the length of time may be longer, i.e., more than four weeks. During the time, the dose can be reduced by 10%-100%. For example, the dose is reduced by 10%, 15%, 20%, 25%, 30%, 35%, 40%, 45%, 50%, 55%, 60%, 65%, 70%, 75%, 80%, 85%, 90%, 95%, or 100%.

In practice, there are situations in which the activity of LPA of a patient should be enhanced for certain purposes, such as, to assist with would healing. In these situations, the dose of administered drug may be also reduced or suspended for a certain length of time. The same as the situation above, the length of time may be 2 days to 1 year. In one embodiment, the length of time is 2 days to a week, including 3 days, 4 days, 5 days, and 6 days. In another embodiment, the length of time is within two weeks, such as 10 days and 12 days. In another embodiment, the length of time is within four weeks, such as 15 days and 20 days. In another embodiment, the patient's condition improves obviously, and the length of time may be longer, i.e., more than four weeks. During the time, the dose can be reduced by 10%-100%. For example, the dose is reduced by 10%, 15%, 20%, 25%, 30%, 35%, 40%, 45%, 50%, 55%, 60%, 65%, 70%, 75%, 80%, 85%, 90%, 95%, or 100%. The normal dosing schedule may be reinstated once the situation requiring enhanced LPA activity is alleviated.

Once the patient's condition is improved, usually, there is a maintenance dose if necessary. After then, the dosage or the frequency of administration, or both may be reduced so that the improved condition is retained. In some embodiments, there are requirements of intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated.

For practical use, an effective amount of the compound is administered to the patient singly. Preferably, a suitable daily dosage of the present compound is about 0.01 to about 10 mg/kg per body weight, that is, the daily dosage suitable for, for example, human being is about 0.5 mg to about 1000 mg. The daily dosage is conveniently administered once or in divided doses, continually or continuously. Once the daily dosage is administered multiple times, for example but not limited to two, three or four times a day, the compound is administered every 6, 8 or 12 hours. The daily dosage may be administered in extended release form and/or in oral administration form with about 1 to 500 mg active ingredient. In certain embodiments, the daily dosage, unit dosage or amount of active ingredient may vary depending on a number of variables in regard to an individual treatment regime, such as the activity of the compound used, the disease or condition to be treated, the mode of administration, the requirements of the individual subject, the severity of the disease or condition being treated, and the judgment of the practitioner.

Besides, the daily dosage amount is relative to toxicity and therapeutic efficacy of such therapeutic regimens, which are determined by standard pharmaceutical procedures in cell cultures or experimental animals, including, but not limited to, the determination of the LD50 and the ED50. The dose ratio between the toxic and therapeutic effects is the therapeutic index and it is expressed as the ratio between LD50 and ED50. In certain embodiments, the data obtained from cell culture assays and animal studies are used in formulating the therapeutically effective daily dosage range and/or the therapeutically effective unit dosage amount for use in human subjects, including humans. In some embodiments, the daily dosage amount of the compounds described herein lies within a range of circulating concentrations that include the ED50 with minimal toxicity. In certain embodiments, the daily dosage range and/or the unit dosage amount varies within this range depending upon the dosage form employed and the route of administration utilized.

In one aspect, the human subject described herein is diagnosed as having heart fibrosis; joint fibrosis; eye fibrosis; muscle fibrosis; lung fibrosis, including but not limited to idiopathic pulmonary fibrosis, lung fibrosis caused by radiation or drug, acute or chronic lung injury and acute respiratory distress that are caused by bacterial pneumonia, viral pneumonia, trauma, ventilator, non-pulmonary sepsis; kidney fibrosis, including but not limited to fibrosis after glomerulonephritis caused by systemic inflammatory diseases such as lupus and scleroderma, diabetes, glomerular nephritis, focal segmental glomerular sclerosis, IgA nephropathy, hypertension, and allograft; liver fibrosis, including but not limited to cirrhosis, alcohol induced liver fibrosis, nonalcoholic steatohepatitis (NASH), biliary duct injury, primary biliary cirrhosis, infection or viral induced liver fibrosis (e.g., chronic HBV or HCV infection), and autoimmune hepatitis; GI track fibrosis, including but not limited to scleroderma, and radiation induced GI track fibrosis; head and neck fibrosis, including but not limited to fibrosis of radiation induced; corneal scarring, e.g., LASIK (laser-assisted in situ keratomileusis) surgery, corneal transplant, and trabeculectomy; skin fibrosis, including but not limited to atopic dermatitis, bullous disorders, psoriatic lesions, dermatitis, contact dermatitis, eczema, rosacea, abnormal wound healing, and excessive scarring; or other fibrotic diseases, including but not limited to scleroderma, spinal cord injury induced fibrosis, myelofibrosis, atherosclerosis, vascular restenosis, sarcoidosis, and other connective tissue diseases.

In another aspect, the human subject is diagnosed as having cancer, including but is not limited to brain, breast, bladder, colorectal, endometrium, kidney, lung, lymphatic tissue, ovary, pancreas, thyroid, prostate, skin or blood tumors at any stage, as well as tumor invasion and metastases.

In yet another aspect, the human subject is diagnosed as having pain, including acute pain or chronic pain, preferably, neuropathic pain or cancer pain.

In certain instances, it is appropriate to administer the compound in combination with another therapeutic agent.

In one embodiment, the therapeutic efficacy of an LPA receptor antagonist compound is enhanced by administration of an adjuvant that by itself does not have efficacy.

In some embodiments, the benefit experienced by a patient is enhanced by administering one of the compounds described herein with another therapeutic agent (which also includes a therapeutic regimen) that also has therapeutic efficacy. In one specific embodiment, the compound is co-administered with a second therapeutic agent, wherein the compound and the second therapeutic agent modulate different aspects of the disease, disorder or condition being treated, thereby providing a greater overall benefit than administration of either therapeutic agent alone. In any disease or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compound disclosed herein is administered in combination with one or more additional agent, such as an adjuvant, or an additional therapeutically effective drug, or the like. Therapeutically effective dosages of drugs and other agents for use in combination treatment regimens can be determined by means similar to those set forth hereinabove for the actives themselves. The method of prevention/treatment described herein treatments in which the compound and the second agent being used in combination are administered simultaneously or at different times and/or at decreasing or increasing intervals during the treatment period. It also includes the use of metronomic dosing, or sequential dosing, to minimize the side effect of either drug alone at higher dose. Combination treatment further includes periodic treatments that start and stop at various times to assist with the clinical management of the patient.

For combination therapies described herein, dosages of the co-administered compounds vary depending on the type of the drug combined with, on the specific drug used, on the disease or condition being treated and so on. In one embodiment, one of the therapeutic agents is given in multiple doses, and in another, two (or more if present) are given as multiple doses. In addition, the combination methods, compositions and formulations are not to be limited to the use of only two agents; the use of multiple therapeutic combinations is also envisioned.

The present compound and the combined drugs are administered before, during or after the occurrence of a disease or condition, and the timing of administering the composition containing a compound varies. Thus, in one embodiment, the compounds described herein are used as a prophylactic and are administered continuously to subjects with a tendency to develop conditions or diseases in order to prevent the occurrence of the disease or condition. In another embodiment, the compounds and compositions are administered to a subject during or as soon as the onset of the symptoms. In specific embodiments, a compound described herein is administered as soon as is practicable after the onset of a disease or condition is detected or suspected, and for a length of time necessary for the treatment of the disease.

In one embodiment, the combined therapeutic agent is a "chemotherapy agent". A "chemotherapeutic agent" is a chemical compound useful in the treatment of cancer. Examples are but not limited to: Gemcitabine, Irinotecan, Doxorubicin, 5-Fluorouracil, Cytosine arabinoside ("Ara-C"), Cyclophosphamide, Thiotepa, Busulfan, Cytoxin, TAXOL, Methotrexate, Cisplatin, Melphalan, Vinblastine and Carboplatin.

In some embodiments, the present compound is used in combination with radiation therapy (or radiotherapy). Radiation therapy is the treatment of cancer and other diseases with ionizing radiation. Radiation therapy can be used to treat localized solid tumors, such as cancers of the lung, skin, tongue, larynx, brain, breast, prostate, colon, uterus and/or cervix. The term "radiotherapy" or "ionizing radiation" include all forms of radiation, including but not limited to α, β, and γ radiation and ultraviolet light.

In one aspect, the present compound is administered in combination with one or more anti-fibrotic agent. In some embodiments, the compound is administered with corticosteroids, nonsteroidal anti-inflammatory drugs (NSAIDs), COX-2 specific inhibitors, or pirfenidone.

In one specific embodiment, the compound described herein is administered to a patient in combination with inhaled corticosteroids.

The present invention also provides a pharmaceutical combination, preferably, a kit, comprising a) a first agent which is the compound of the invention as disclosed herein, in free form or in pharmaceutically acceptable salt form, and b) at least one co-agent. In addition, the kit may comprise instructions for its administration.

The combination therapy of the present invention may be used in vitro or in vivo. These processes may involve administering the agents at the same time or within a period of time wherein separate administration of the substances produces a desired therapeutic benefit. This may be achieved by contacting the cell, tissue, or organism with a single composition or pharmacological formulation that includes two or more agents, or by contacting the cell with two or more distinct compositions or formulations, wherein one composition includes one agent and the other includes another. The compound of the present invention may precede, be co-current with and/or follow the other agents by intervals ranging from minutes to weeks. In embodiments where the agents are applied separately to a cell, tissue or organism, a person skilled in the art would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In another embodiment, one or more agents may be administered about between 1 minute to 14 days.

Pharmaceutical formulation described herein is administerable to a subject in a variety of ways by multiple administration routes, including but not limited to, oral, parenteral (e.g., intravenous, subcutaneous, intramuscular), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In yet another aspect, the present invention provides a method of inhibiting the physiological activity of LPA in a human subject comprising administering a therapeutically effective amount of the present compound or a pharmaceutically acceptable salt thereof to the human subject in need thereof.

In yet another aspect, the present invention provides a medicament for treating a LPA-dependent or LPA-mediated disease or condition in a human subject, wherein the medicament comprises a therapeutically effective amount of the compound.

In yet another aspect, the present invention provides a process for preparing the compound of the present invention or the salts or derivatives thereof.

Mostly, the present compound may be prepared by one of the synthetic methodology described in the following examples. In the reactions, some reactive functional groups desired in the final product are protected so that they will not participate in the unwanted reactions, wherein the reactive functional group may be hydroxy, amino, imino, thio or carboxy group. For this purpose, the protecting groups may be used in accordance with standard practice. Such standard practice can be found in T. W. Greene and P. G. M. Wuts in "Protective Groups in Organic Chemistry", John Wiley and Sons, 1991. Besides, suitable leaving groups may be used in the synthetic methodology, such as halogen leaving groups and other conventional leaving groups known in the art. Preferably, the leaving group is chloro or bromo.

The present compound or the salts thereof may also be prepared in the form of hydrates or crystals, wherein the crystals may include solvent for crystallization. It is well known in the art that salts thereof can be converted to compounds in free form by treating with suitable agent. Such suitable agent may be alkali metal carbonate, alkali metal hydrogen carbonate, or alkali metal hydroxide. Preferably, it is potassium carbonate or sodium hydroxide. In specific embodiment, the compound in a base addition salt form may be converted to the corresponding free acid by treating with a suitable acid, such as hydrochloric acid. A person skilled in the art may well know the relationship between the free compounds and their salts, and convert one to the other if necessary. Preferably, it is well known how to get the salts in the purification or identification of the compound as intermediates.

Salts of the present compound with a salt-forming group may be prepared in a manner known in the art. Acid addition salts of compound of Formula (I) or (II) may thus be obtained by treatment with an acid or with a suitable anion exchange reagent. Pharmaceutically acceptable salts of the compound of the invention may be formed as acid addition salts from compound of Formula (I) or (II) with a basic nitrogen atom with organic or inorganic acids.

Preferably, suitable inorganic acids include, but are not limited to, halogen acids, such as hydrochloric acid, sulfuric acid, or phosphoric acid.

Preferably, suitable organic acids include, but are not limited to, carboxylic, phosphoric, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4 aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4 methylbenzenesulfonic acid, methylsulfuric acid, ethylsulfuric acid, dodecylsulfuric acid, N cyclohexylsulfamic acid, N-methyl-, N-ethyl- or N-propyl-sulfamic acid, or other organic protonic acids, such as ascorbic acid.

Alternatively, it is also possible to use pharmaceutically unacceptable salts for isolation or purification, for example picrates or perchlorates. But for therapeutic use, only pharmaceutically acceptable salts or free compounds are employed, where applicable in the form of pharmaceutical preparations.

In yet another embodiment, compound of the present invention in unoxidized form may be prepared from N-oxides of compound of the invention by treating with a reducing agent in a suitable inert organic solvent at 0 to 80° C. Preferably, the reducing agent is sulfur, sulfur dioxide, triphenyl phosphine, lithium borohydride, sodium borohydride, phosphorus trichloride, tribromide, or the like. Preferably, the invert organic solvent is acetonitrile, ethanol, aqueous dioxane, or the like.

In another embodiment, prodrug derivatives of the compound of the present invention may be prepared by methods known in the art (for further details see Saulnier et al., (1994), Bioorganic and Medicinal Chemistry Letters, Vol. 4, p. 1985). In a preferable embodiment, an appropriate prodrug may be prepared by reacting a non-derivatized compound of the invention with a suitable carbamylating agent such as 1,1-acyloxyalkylcarbanochloridate, para-nitrophenyl carbonate, or the like.

In yet another embodiment, protected derivatives of the compound of the present invention may be made by means known in the art. A detailed description of techniques applicable to the creation of protecting groups and their removal may be found in T. W. Greene, "Protecting Groups in Organic Chemistry", 3rd edition, John Wiley and Sons, Inc., 1999.

In yet another embodiment, the present invention also provides the individual stereoisomers of the compound. The process of preparing the individual stereoisomers includes reacting a racemic mixture of the compound with an optically active resolving agent to form a pair of diastereomers, separating the diastereomers and recovering the optically pure enantiomers. Enantiomers may be separated by using covalent diastereomeric derivatives of the compound of the present invention, or by using dissociable complexes such as crystalline diastereomeric salts. Diastereomers have distinct physical properties such as melting points, boiling points, solubilities and reactivity, so that they may be readily separated by taking advantage of these dissimilarities. Preferably, the diastereomers may be separated by fractionated crystallization, chromatography, or by separation/resolution techniques based upon differences in solubility. Then by using any practical means that would not result in racemization and by using the resolving agent, a person skilled in the art can easily get the optically pure enantiomer. There is a more detailed description of the techniques applicable to the resolution of stereoisomers of compounds from their racemic mixture in Jean Jacques, Andre Collet, Samuel H. Wilen, "Enantiomers, Racemates and Resolutions", John Wiley And Sons, Inc., 1981.

In conclusion, the compound of the present invention could be made by the process described in the Examples;

optionally a pharmaceutically acceptable salt may be converted from the compound of the present invention;

optionally a pharmaceutically acceptable N-oxide may be converted from an unoxidized form of the compound the present invention;

optionally an individual isomer of the compound of the present invention is resolved from a mixture of isomers; and optionally a pharmaceutically acceptable prodrug derivative may be converted from a non-derivatized compound of the present invention.

The above methods and transformations are just for purpose of representative. A person skilled in the art can easily know the methods of preparation in the art. All the methods can be used herein.

DETAILED DESCRIPTION OF PREFERRED EMBODIMENTS

The present invention is further exemplified, but not limited, by the following and Examples that illustrate the preparation of the compounds of the invention.

| Abbreviation | Definition or Explanation |
|---|---|
| DCM | Dichloromethane |
| DIEA | N,N'-Diisopropylethylamine |
| DMF | N,N-Dimethylformamide |
| eq. | equivalents |
| TEA | Triethylamine |
| THF | Tetrahydrofuran |
| RT | Room Temperature |
| EA | Ethyl acetate |
| DPPA | Diphenylphosphoryl azide |

Example 1

Process of Synthesis of Compound 1

1-(2-chlorophenyl)ethyl(3-methyl-5-(4-(methylsulfonamido)phenyl)isoxazol-4-yl)carbamate

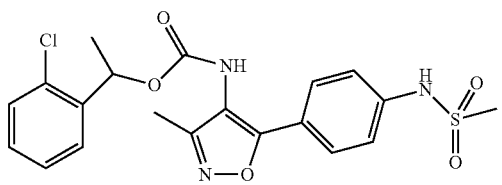 [SMILES: Cc1noc(-c2ccc(NS(C)(=O)=O)cc2)c1NC(=O)OC(C)c1ccccc1Cl]

Step 1:

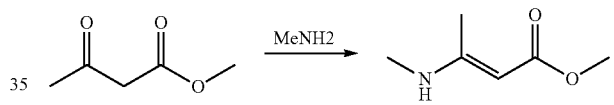

Methyl acetoacetate (11.6 g, 100 mmol) was dissolved in 20 mL MeOH. Methylamine (33 wt % in absolute ethanol, 18.7 mL, 150 mmol) was added into the solution very slowly at room temperature, and the reaction was stirred for 2 hours. The solvent was removed under the vacuum to give the final product (E)-methyl 3-(methylamino)but-2-enoate as white solid without further purification (12.9 g).

Step 2:

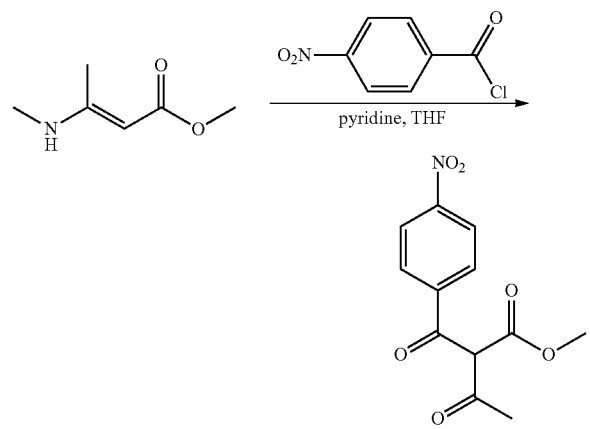

(E)-methyl 3-(methylamino)but-2-enoate (12.9 g, 100 mmol) was dissolved in 300 mL anhydrous THF and 12 mL pyridine was added into the solution dropwise. The reaction was cooled in ice bath, and 4-nitrobenzoyl chloride (18.7 mL in 50 mL anhydrous THF) was added into the solution slowly. The reaction was warmed up to room temperature and stirred for overnight. After adding 300 mL water into the reaction, the solution was extracted by ethyl acetate for 3 times. The combined organic layer was further washed with water and brine, dried over Na2SO4, and removed under the vacuum to give methyl 2-(4-nitrobenzoyl)-3-oxobutanoate as the solid without further purification (25.2 g, 95% yield).

Step 3:

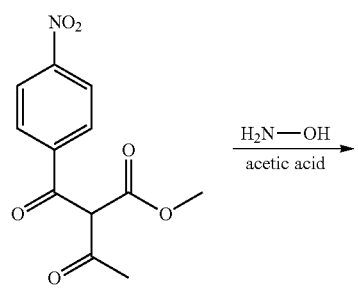

Methyl 2-(4-nitrobenzoyl)-3-oxobutanoate (20.0 g, 75.47 mmol) was dissolved in acetic acid (70 mL), and followed by adding hydroxylamine hydrochloride (5.10 g, 73.27 mmol). The reaction was stirred at 115° C. for 2 hours. After cooling the reaction to the RT, 400 mL saturated NaHCO3 was added into the solution and extracted by ethyl acetate for 3 times. The combined organic layer was washed by brine and dried over Na2SO4, and removed under the vacuum. The crude product was further purified by flash chromatography using EA/Hexane=1:9 to give methyl 3-methyl-5-(4-nitrophenyl) isoxazole-4-carboxylate (16.4 g, 83% yield). MS m/z 263.1 (M+1).

Step 4:

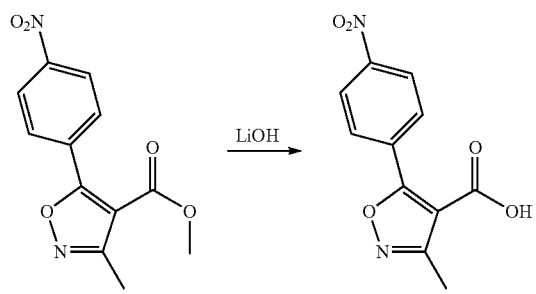 [SMILES: COC(=O)c1c(C)noc1-c1ccc([N+](=O)[O-])cc1 ; "LiOH" ; Cc1noc(-c2ccc([N+](=O)[O-])cc2)c1C(=O)O]

Methyl 3-methyl-5-(4-nitrophenyl)isoxazole-4-carboxylate (13.1 g, 50 mmol) was dissolved in 150 mL dioxane, and followed by adding 125 mL lithium hydroxide (2N). The reaction was stirred at RT for overnight and neutralized by 6N HCl till pH<6. After removing the dioxane under the vacuum, the water solution was extracted by DCM for 3 times. The combined organic layer was washed by brine and dried over Na2SO4. After removing the solvent under the vacuum, the product 3-methyl-5-(4-nitrophenyl)isoxazole-4-carboxylic acid was used in next step reaction without further purification (10.66 g, 86% yield). MS m/z 249.1 (M+1).

Step 5:

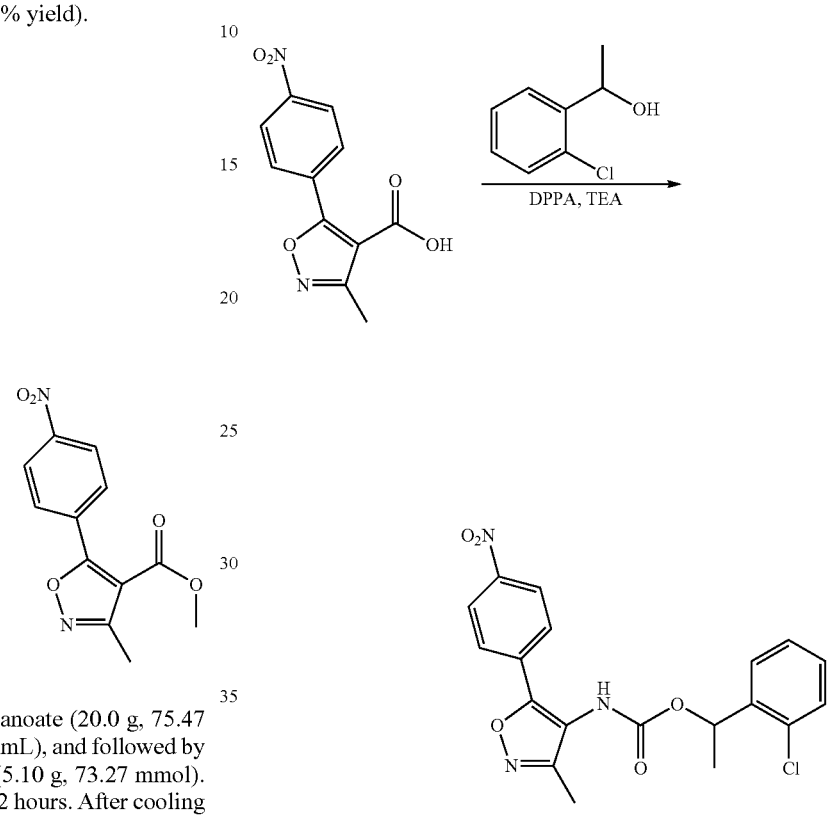

3-methyl-5-(4-nitrophenyl)isoxazole-4-carboxylic acid (2.5 g, 10 mmol) was dissolved in 30 mL toluene in a sealed tube, and followed by adding 1-(2-chlorophenyl)ethanol (1.88 g, 12 mmol), triethylamine (2.02 g, 20 mmol) and diphenylphosphoryl azide (4.13 g, 15 mmol). The reaction was stirred at 125° C. for 2 hours. After cooling down the reaction to RT, the solvent was removed under the vacuum. The crude product was purified by flash chromatography using EA/Hexane (1:1) to get 1-(2-chlorophenyl)ethyl(3-methyl-5-(4-nitrophenyl)isoxazol-4-yl)carbamate (2.60 g, 65% yield). MS m/z 402.1 (M+1).

Step 6:

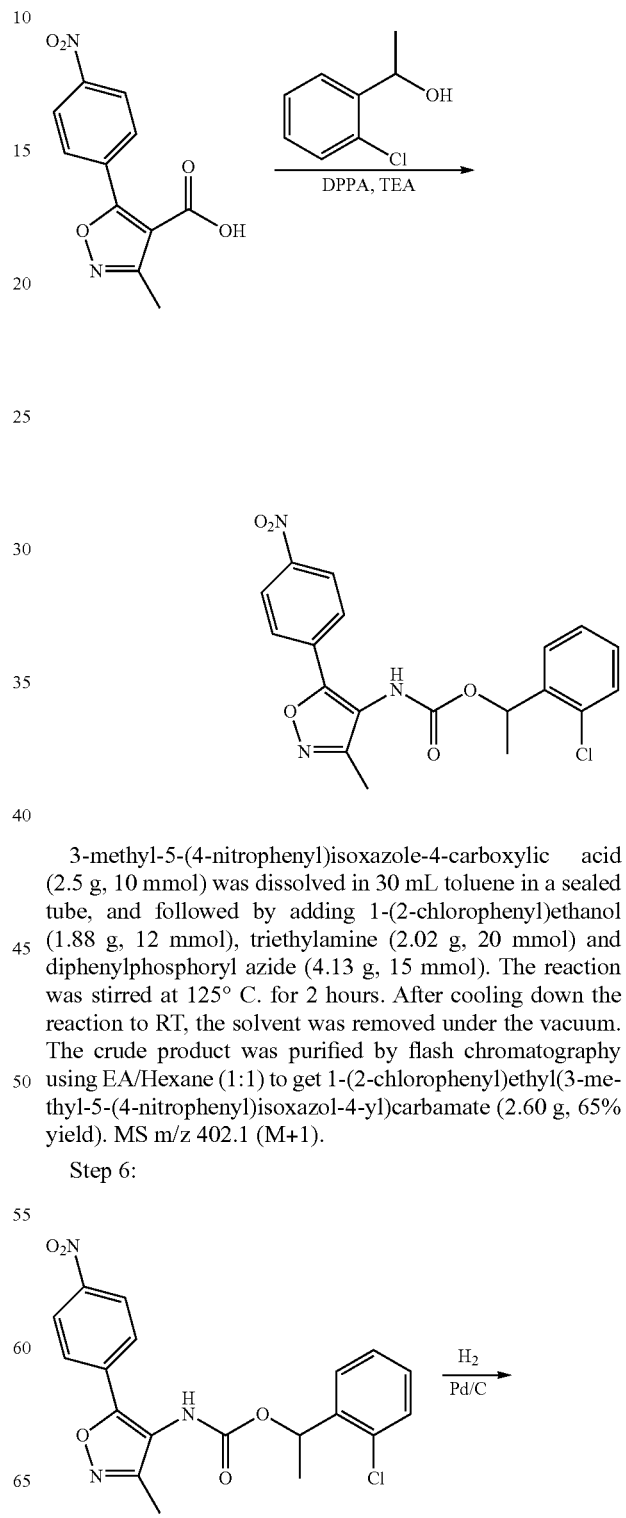

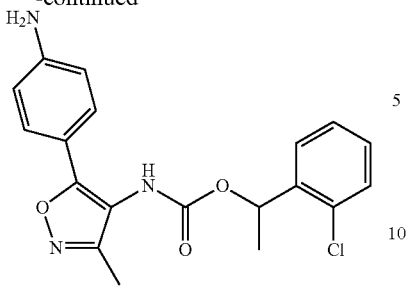

1-(2-chlorophenyl)ethyl(3-methyl-5-(4-nitrophenyl)isoxazol-4-yl)carbamate (2.60 g, 6.48 mmol) was dissolved in 100 mL ethanol, followed by adding 260 mg Pd/C (10% w/w). The reaction was stirred at RT under a hydrogen balloon for 4 hours. After filtering through a pad of celite, the solvent was removed under the vacuum to get the product 1-(2-chlorophenyl)ethyl(5-(4-aminophenyl)-3-methylisoxazol-4-yl)carbamate without further purification. MS m/z 372.1 (M+1).

Step 7:

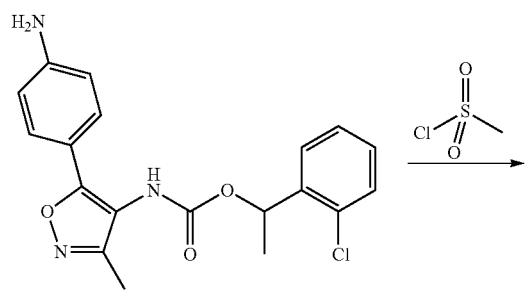

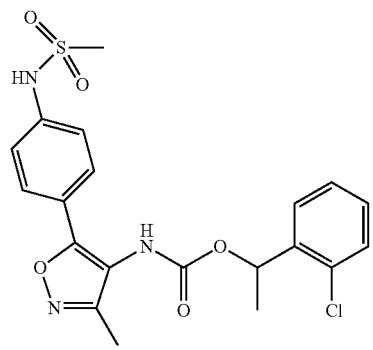

1-(2-chlorophenyl)ethyl(5-(4-aminophenyl)-3-methylisoxazol-4-yl)carbamate (50 mg, 0.13 mmol) was dissolved in 5 mL anhydrous DCM, followed by adding DIEA (47 μl, 0.26 mmol). Methanesulfonyl chloride (16.8 mg, 0.15 mmol) was added into the solution and the reaction was stirred at RT for 2 hours. After removing the solvent under the vacuum, the crude product was further purified by prep-TLC plate using 5% MeOH in DCM to get the final product 1-(2-chlorophenyl)ethyl(3-methyl-5-(4-(methylsulfonamido)phenyl)isoxazol-4-yl)carbamate (49 mg, 82% yield). 1H NMR (400 MHz, CDCl3): δ1.28 (d, J=7.2Hz, 3H), 2.23 (s, 3H), 3.00 (s, 3H), 4.14 (q, J=7.2Hz, 1H), 5.32 (s, 1H), 7.13 (d, J=8.4Hz, 2H), 7.34-7.48 (m, 5H), 7.57 (d, J=7.6Hz, 1H), 9.02 (s, 1H), 9.61 (s, 1H) MS m/z 404.2 (M+1). MS m/z 450.2 (M+1).

| Compound No. | Structure | MS m/z (M + 1) |
|---|---|---|
| 2 | 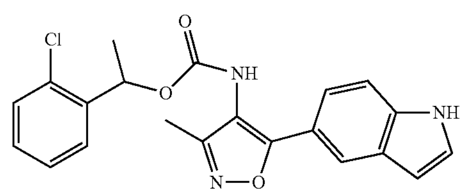 [SMILES: Cc1noc(-c2ccc3[nH]ccc3c2)c1NC(=O)OC(C)c1ccccc1Cl] | 396.1 |
| 3 | 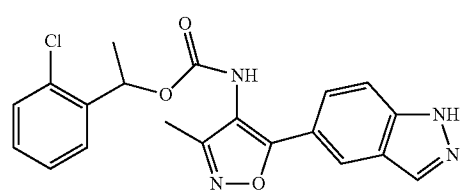 [SMILES: Cc1noc(-c2ccc3[nH]ncc3c2)c1NC(=O)OC(C)c1ccccc1Cl] | 397.1 |
| 4 | 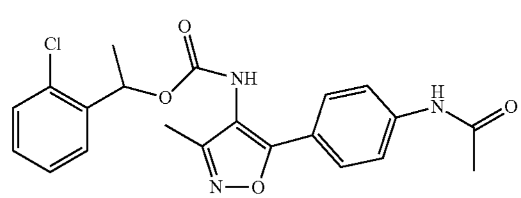 [SMILES: CC(=O)Nc1ccc(-c2onc(C)c2NC(=O)OC(C)c2ccccc2Cl)cc1] | 414.2 |

-continued

| Compound No. | Structure | MS m/z (M + 1) |
|---|---|---|
| 5 | 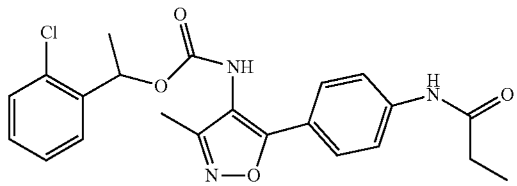 [SMILES: CCC(=O)Nc1ccc(-c2onc(C)c2NC(=O)OC(C)c2ccccc2Cl)cc1] | 428.2 |
| 6 | 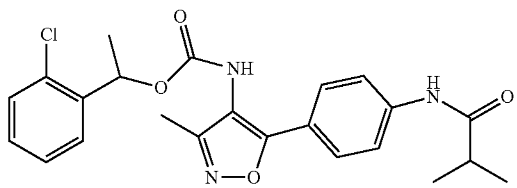 [SMILES: Cc1noc(-c2ccc(NC(=O)C(C)C)cc2)c1NC(=O)OC(C)c1ccccc1Cl] | 442.2 |
| 7 | 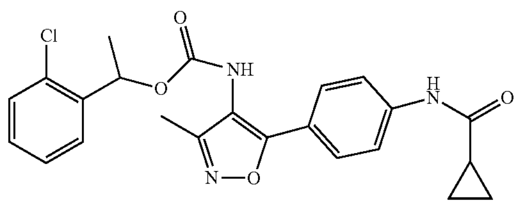 [SMILES: Cc1noc(-c2ccc(NC(=O)C3CC3)cc2)c1NC(=O)OC(C)c1ccccc1Cl] | 440.2 |
| 8 | 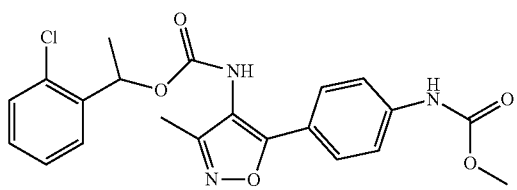 | 430.2 |
| 9 | 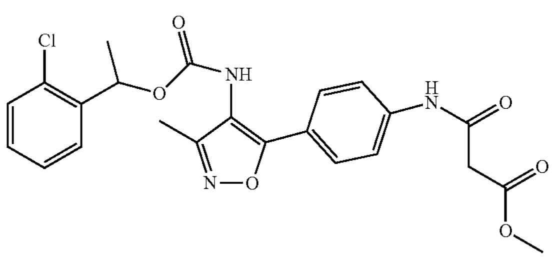 [SMILES: COC(=O)CC(=O)Nc1ccc(-c2onc(C)c2NC(=O)OC(C)c2ccccc2Cl)cc1] | 472.2 |
| 10 | 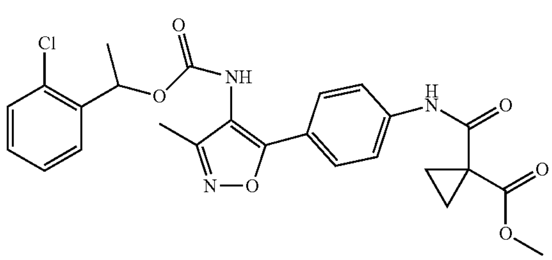 [SMILES: COC(=O)C1(C(=O)Nc2ccc(-c3onc(C)c3NC(=O)OC(C)c3ccccc3Cl)cc2)CC1] | 498.2 |
| 11 | 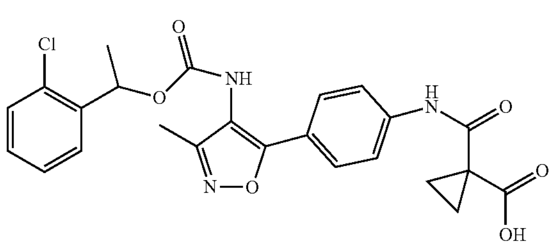 [SMILES: Cc1noc(-c2ccc(NC(=O)C3(C(=O)O)CC3)cc2)c1NC(=O)OC(C)c1ccccc1Cl] | 484.2 |

-continued

| Compound No. | Structure | MS m/z (M + 1) |
|---|---|---|
| 12 | 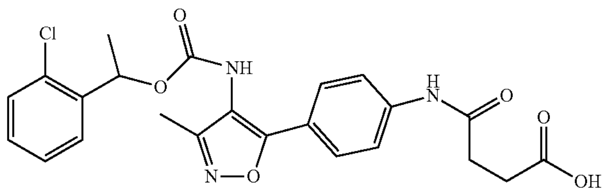 [SMILES: Cc1noc(-c2ccc(NC(=O)CCC(=O)O)cc2)c1NC(=O)OC(C)c1ccccc1Cl] | 472.2 |
| 13 | 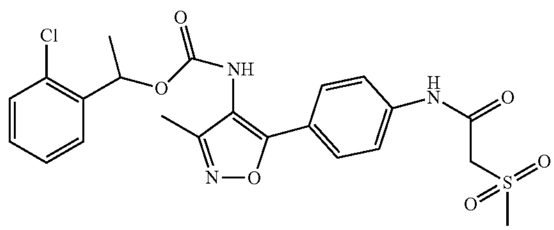 [SMILES: Cc1noc(-c2ccc(NC(=O)CS(C)(=O)=O)cc2)c1NC(=O)OC(C)c1ccccc1Cl] | 492.2 |
| 14 | 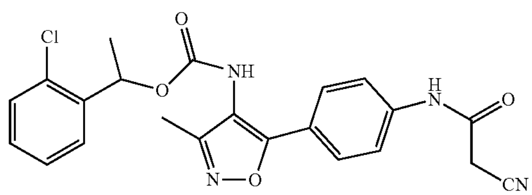 [SMILES: Cc1noc(-c2ccc(NC(=O)CC#N)cc2)c1NC(=O)OC(C)c1ccccc1Cl] | 439.2 |
| 15 | 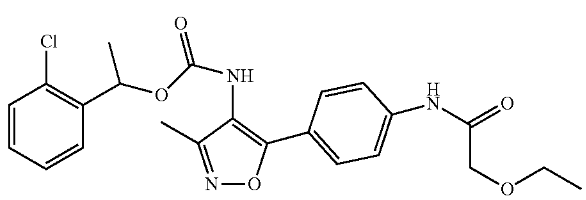 [SMILES: CCOCC(=O)Nc1ccc(-c2onc(C)c2NC(=O)OC(C)c2ccccc2Cl)cc1] | 458.2 |
| 16 | 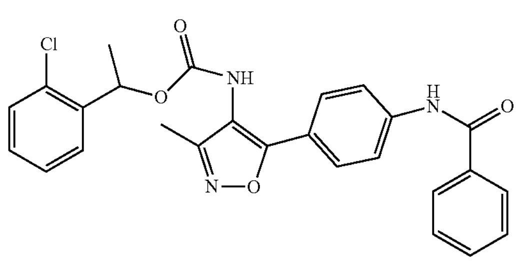 [SMILES: Cc1noc(-c2ccc(NC(=O)c3ccccc3)cc2)c1NC(=O)OC(C)c1ccccc1Cl] | 476.2 |
| 17 | 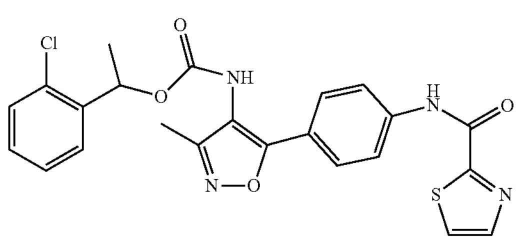 [SMILES: Cc1noc(-c2ccc(NC(=O)c3nccs3)cc2)c1NC(=O)OC(C)c1ccccc1Cl] | 483.2 |

-continued

| Compound No. | Structure | MS m/z (M + 1) |
|---|---|---|
| 18 | 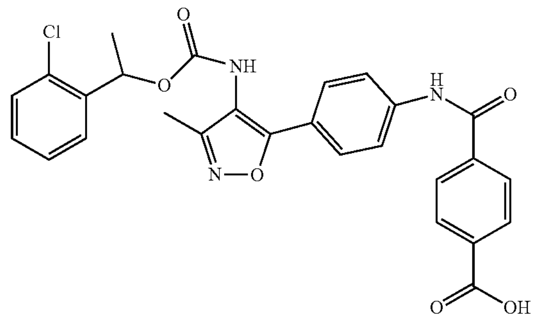 [SMILES: Cc1noc(-c2ccc(NC(=O)c3ccc(C(=O)O)cc3)cc2)c1NC(=O)OC(C)c1ccccc1Cl] | 520.2 |
| 19 | 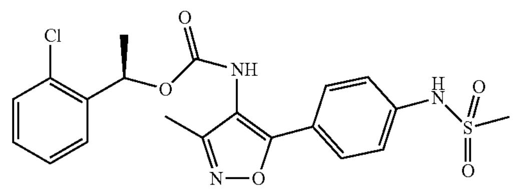 [SMILES: Cc1noc(-c2ccc(NS(C)(=O)=O)cc2)c1NC(=O)O[C@H](C)c1ccccc1Cl] | 450.2 |
| 20 | 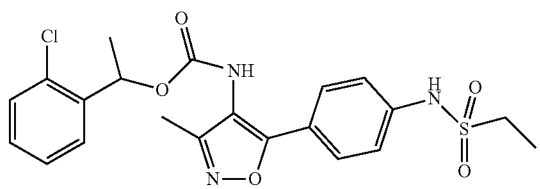 [SMILES: CCS(=O)(=O)Nc1ccc(-c2onc(C)c2NC(=O)OC(C)c2ccccc2Cl)cc1] | 464.2 |
| 21 | 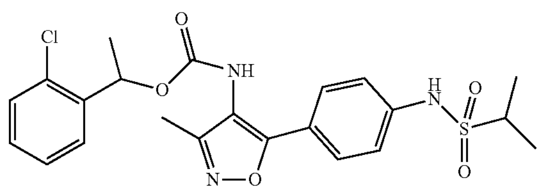 [SMILES: Cc1noc(-c2ccc(NS(=O)(=O)C(C)C)cc2)c1NC(=O)OC(C)c1ccccc1Cl] | 478.2 |
| 22 | 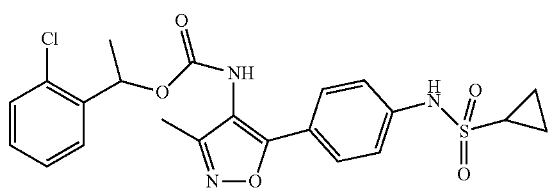 [SMILES: Cc1noc(-c2ccc(NS(=O)(=O)C3CC3)cc2)c1NC(=O)OC(C)c1ccccc1Cl] | 476.2 |
| 23 | 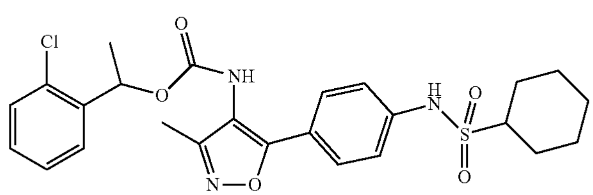 [SMILES: Cc1noc(-c2ccc(NS(=O)(=O)C3CCCCC3)cc2)c1NC(=O)OC(C)c1ccccc1Cl] | 518.2 |
| 24 | 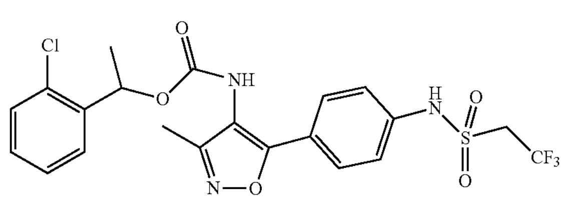 [SMILES: Cc1noc(-c2ccc(NS(=O)(=O)CC(F)(F)F)cc2)c1NC(=O)OC(C)c1ccccc1Cl] | 518.2 |

| Compound No. | Structure | MS m/z (M + 1) |
|---|---|---|
| 25 | 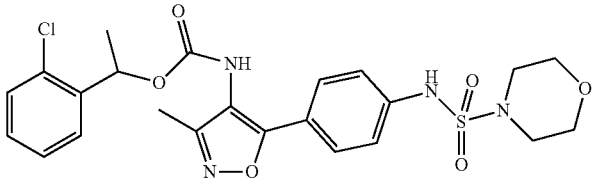 [SMILES: Cc1noc(-c2ccc(NS(=O)(=O)N3CCOCC3)cc2)c1NC(=O)OC(C)c1ccccc1Cl] | 521.1 |
| 26 | 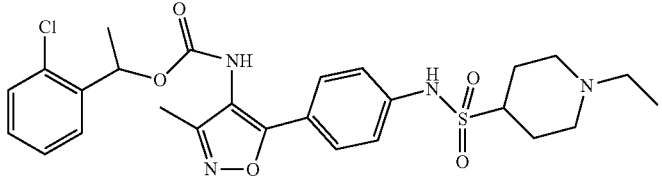 [SMILES: CCN1CCC(S(=O)(=O)Nc2ccc(-c3onc(C)c3NC(=O)OC(C)c3ccccc3Cl)cc2)CC1] | 547.2 |
| 27 | 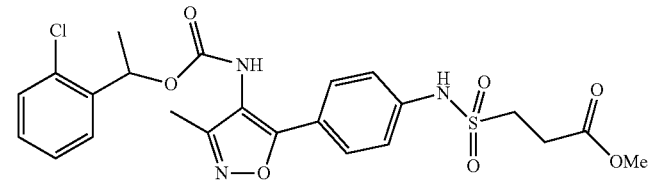 [SMILES: COC(=O)CCS(=O)(=O)Nc1ccc(-c2onc(C)c2NC(=O)OC(C)c2ccccc2Cl)cc1] | 522.2 |
| 28 | 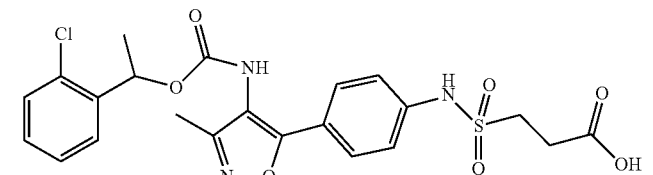 | 508.2 |
| 29 | 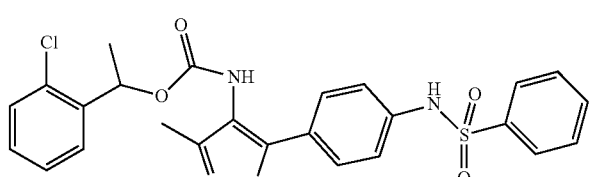 | 512.2 |
| 30 | 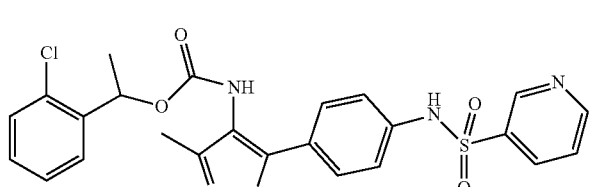 | 513.2 |
| 31 | 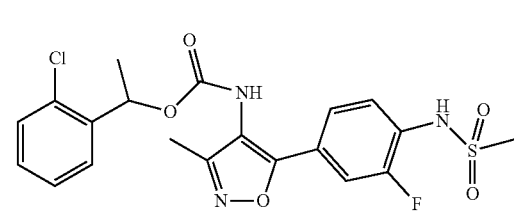 [SMILES: Cc1noc(-c2ccc(NS(C)(=O)=O)c(F)c2)c1NC(=O)OC(C)c1ccccc1Cl] | 468.2 |

-continued
| Compound No. | Structure | MS m/z (M + 1) |
|---|---|---|
| 32 | 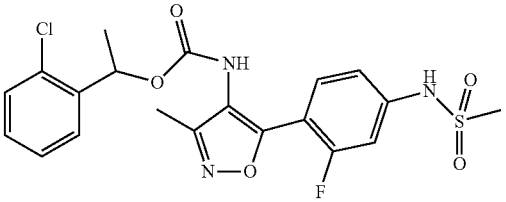 [SMILES: Cc1noc(-c2ccc(NS(C)(=O)=O)cc2F)c1NC(=O)OC(C)c1ccccc1Cl] | 468.2 |
| 33 | 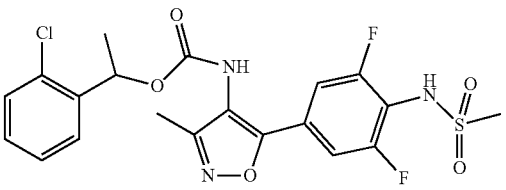 [SMILES: Cc1noc(-c2cc(F)c(NS(C)(=O)=O)c(F)c2)c1NC(=O)OC(C)c1ccccc1Cl] | 486.2 |
| 34 | 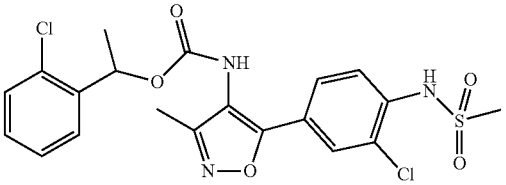 [SMILES: Cc1noc(-c2ccc(NS(C)(=O)=O)c(Cl)c2)c1NC(=O)OC(C)c1ccccc1Cl] | 484.2 |
| 35 | 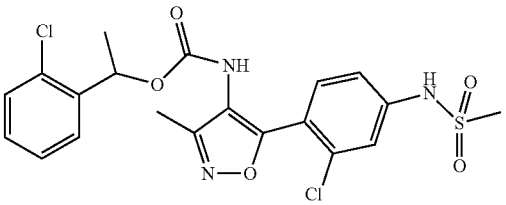 | 484.2 |
| 36 | 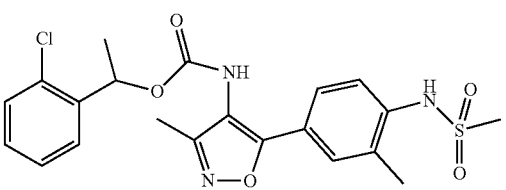 [SMILES: Cc1cc(-c2onc(C)c2NC(=O)OC(C)c2ccccc2Cl)ccc1NS(C)(=O)=O] | 464.2 |
| 37 | 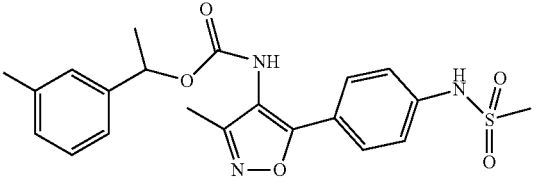 | 450.2 |
| 38 | 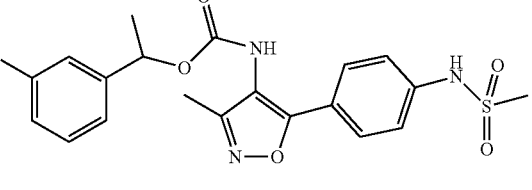 | 434.2 |

-continued

| Compound No. | Structure | MS m/z (M + 1) |
|---|---|---|
| 39 | 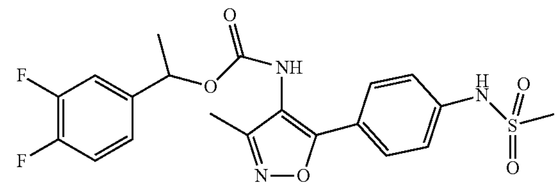 [SMILES: Cc1noc(-c2ccc(NS(C)(=O)=O)cc2)c1NC(=O)OC(C)c1ccc(F)c(F)c1] | 452.2 |
| 40 | 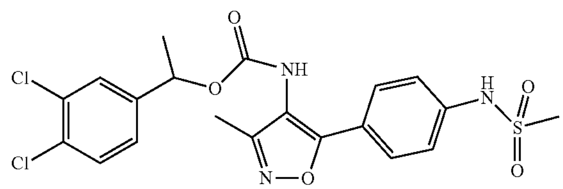 [SMILES: Cc1noc(-c2ccc(NS(C)(=O)=O)cc2)c1NC(=O)OC(C)c1ccc(Cl)c(Cl)c1] | 484.2 |
| 41 | 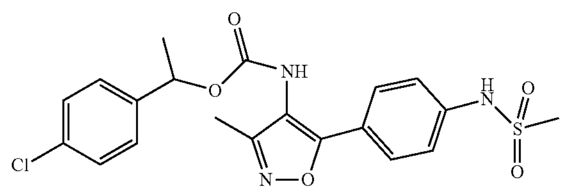 [SMILES: Cc1noc(-c2ccc(NS(C)(=O)=O)cc2)c1NC(=O)OC(C)c1ccc(Cl)cc1] | 450.2 |
| 42 | 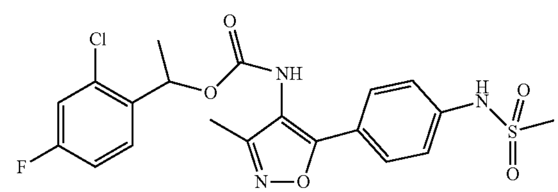 [SMILES: Cc1noc(-c2ccc(NS(C)(=O)=O)cc2)c1NC(=O)OC(C)c1ccc(F)cc1Cl] | 468.2 |
| 43 | 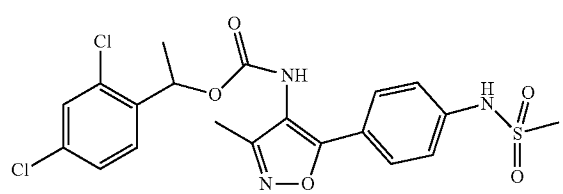 [SMILES: Cc1noc(-c2ccc(NS(C)(=O)=O)cc2)c1NC(=O)OC(C)c1ccc(Cl)cc1Cl] | 484.2 |
| 44 | 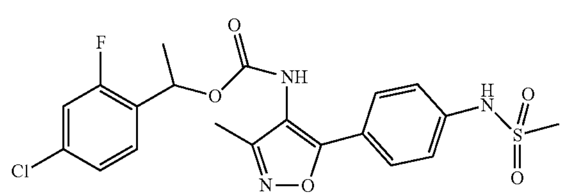 | 468.2 |
| 45 | 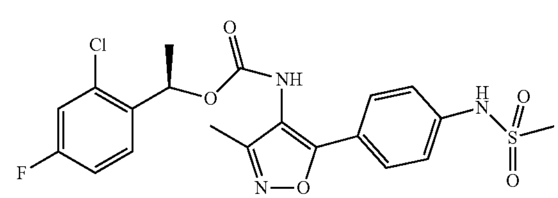 [SMILES: Cc1noc(-c2ccc(NS(C)(=O)=O)cc2)c1NC(=O)O[C@H](C)c1ccc(F)cc1Cl] | 468.2 |

| Compound No. | Structure | MS m/z (M + 1) |
|---|---|---|
| 46 | 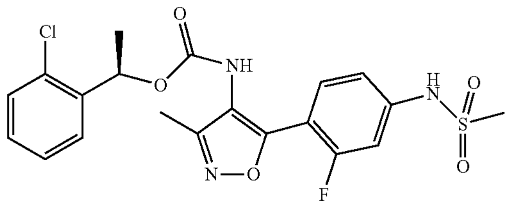 [SMILES: Cc1noc(-c2ccc(NS(C)(=O)=O)cc2F)c1NC(=O)O[C@H](C)c1ccccc1Cl] | 468.2 |
| 47 | 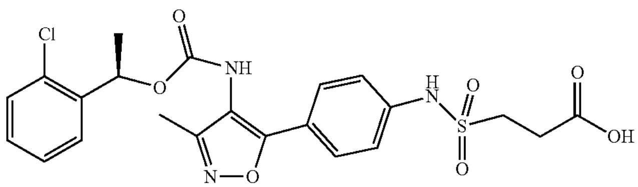 [SMILES: Cc1noc(-c2ccc(NS(=O)(=O)CCC(=O)O)cc2)c1NC(=O)O[C@H](C)c1ccccc1Cl] | 508.2 |
| 48 | 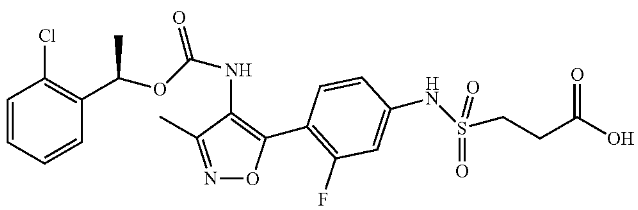 [SMILES: Cc1noc(-c2ccc(NS(=O)(=O)CCC(=O)O)cc2F)c1NC(=O)O[C@H](C)c1ccccc1Cl] | 526.2 |
| 49 | 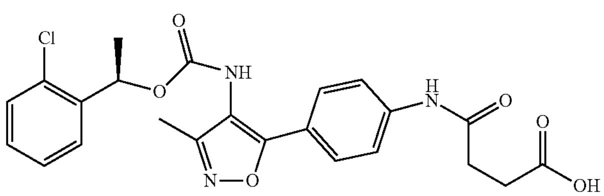 [SMILES: Cc1noc(-c2ccc(NC(=O)CCC(=O)O)cc2)c1NC(=O)O[C@H](C)c1ccccc1Cl] | 472.2 |
| 50 | 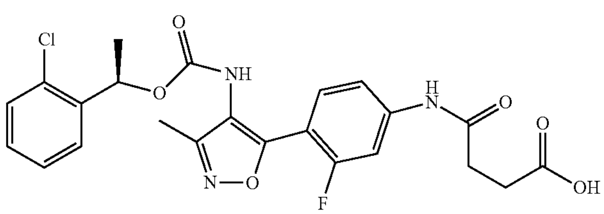 [SMILES: Cc1noc(-c2ccc(NC(=O)CCC(=O)O)cc2F)c1NC(=O)O[C@H](C)c1ccccc1Cl] | 490.2 |

Example 2

Molecular Cloning

A cDNA encoding the human LPA1 receptor was cloned by PCR from cDNA clone obtained from commercial sources. The nucleotide sequence was determined by sequencing and confirmed to be identical to the published human LPA1 sequence (An, 1997). The 1.1 kb cDNA encoding the full-length coding region of human LPA1 was subcloned into the pRK5 human subject ian expression vector. Transfection of the cDNA into HEK293 or CHO cells is performed by using LipofectAmine 2000 (Invitrogen, USA).

The full-length cDNA fragments for human LPA2 and LPA3 were obtained by PCR similarly and subcloned into pCDNA3.1 expression vector.

Example 3

LPA Receptor Assays

Transfected cells were cultured and subjected to LPA-induced SRE-luciferase reporter gene assay by using generally described methods (An, 1997). Intact HEK293 or CHO cells expressing the recombinant human LPA1 receptor were subjected to a [3H]-LPA ligand binding assay as described (An, 1998).

All compounds presented in the patent have IC50<20 μM in the calcium flux assay. Selective examples were listed in the table below.

| Compound ID Number | IC50 (μM) |
|---|---|
| 1 | 0.09 |
| 3 | 0.55 |
| 7 | 1.15 |
| 12 | 0.07 |
| 16 | 2.20 |
| 19 | 0.055 |
| 28 | 0.11 |
| 32 | 0.07 |
| 42 | 0.06 |
| 50 | 0.07 |

Example 4

Bleomycin-Induced Lung Fibrosis Model in Mice

Female Kunming strain mice (weighing 20-30 g) mice were randomly divided into the following four groups: (i) saline group (n=8); (ii) Bleomycin alone group (n=8) in which mice were intratracheally instilled with 5 mg/kg Bleomycin sulfate solution (Nippon Kayaku, Tokyo, Japan) (2.5 mg/ml in 0.9% saline); (iii) Bleomycin+compound group (n=12) in which mice were intraperitoneally (i.p.) given compounds were given 2 days prior to Bleomycin instillation and daily after Bleomycin instillation until the end of the treatment; and (iv) compound alone group (n=12) in which mice were given compound i.p. On day 17 after administration, animals were euthanized, and pulmonary fibrosis was assessed based on lung hydroxyproline content and histological changes. The lung tissues were fixed with a buffered 15% formalin solution for 1 week, embedded in paraffin, and then sectioned at 3 mm. The sections were stained with hematoxylin and eosin (H&E) and alpha-smooth muscle actin (alpha-SMA) expression was detected by immunohistochemical assay.

REFERENCES

An S, Bleu T, Hallmark O G, Goetzl E J. Characterization of a novel subtype of human G protein-coupled receptor for lysophosphatidic acid. J Biol Chem. 1998 Apr. 3; 273(14): 7906-10.

An S, Dickens M A, Bleu T, Hallmark O G, Goetzl E J. Molecular cloning of the human Edg2 protein and its identification as a functional cellular receptor for lysophosphatidic acid. Biochem Biophys Res Commun 1997 Feb. 24; 231(3):619-22.

Bandoh K, Aoki J, Hosono H, Kobayashi S, Kobayashi T, Murakami-Murofushi K, Tsujimoto M, Arai H, Inoue K. Molecular cloning and characterization of a novel human G-protein-coupled receptor, EDG7, for lysophosphatidic acid. J Biol Chem. 1999 Sep. 24; 274(39):27776-85.

Chun J, Hla T, Lynch K R, Spiegel S, Moolenaar W H. International Union of Basic and Clinical Pharmacology. LXXVIII. Lysophospholipid receptor nomenclature. Pharmacol Rev. 2010 December; 62(4):579-87.

Hahn A, Heusinger-Ribeiro J, Lanz T, Zenkel S, Goppelt-Struebe M. Induction of connective tissue growth factor by activation of heptahelical receptors. Modulation by Rho proteins and the actin cytoskeleton. J Biol Chem. 2000 Dec. 1; 275(48):37429-35.

Inoue M, Rashid M H, Fujita R, Contos J J, Chun J, Ueda H. Initiation of neuropathic pain requires lysophosphatidic acid receptor signaling. Nat Med. 2004 July; 10(7):712-8.

Jeon E S, Moon H J, Lee M J, Song H Y, Kim Y M, Cho M, Suh D S, Yoon M S, Chang C L, Jung J S, Kim J H. Cancer-derived lysophosphatidic acid stimulates differentiation of human mesenchymal stem cells to myofibroblast-like cells. Stem Cells. 2008 March; 26(3):789-97.

Mills G B, Moolenaar W H. The emerging role of lysophosphatidic acid in cancer. Nat Rev Cancer. 2003 August; 3(8):582-91.

Moolenaar W H, van Meeteren L A, Giepmans B N. The ins and outs of lysophosphatidic acid signaling. Bioessays. 2004 August; 26(8):870-81.

Nakanaga K, Hama K, Aoki J. Autotaxin—an LPA producing enzyme with diverse functions. J Biochem. 2010 July; 148(1):13-24.

Pradère J P, Klein J, Grès S, Guigné C, Neau E, Valet P, Calise D, Chun J, Bascands J L, Saulnier-Blache J S, Schanstra J P. LPA1 receptor activation promotes renal interstitial fibrosis. J Am Soc Nephrol. 2007 December; 18(12):3110-8.

Swaney J S, Chapman C, Correa L D, Stebbins K J, Bundey R A, Prodanovich P C, Fagan P, Baccei C S, Santini A M, Hutchinson J H, Seiders T J, Parr T A, Prasit P, Evans J F, Lorrain D S. A novel, orally active LPA(1) receptor antagonist inhibits lung fibrosis in the mouse bleomycin model. Br J Pharmacol. 2010 August; 160(7): 1699-713.

Tager A M, LaCamera P, Shea B S, Campanella G S, Selman M, Zhao Z, Polosukhin V, Wain J, Karimi-Shah B A, Kim N D, Hart W K, Pardo A, Blackwell T S, Xu Y, Chun J, Luster A D. The lysophosphatidic acid receptor LPA1 links pulmonary fibrosis to lung injury by mediating fibroblast recruitment and vascular leak. Nat Med. 2008 January; 14(1):45-54.

Tigyi G. Aiming drug discovery at lysophosphatidic acid targets. Br J Pharmacol. 2010 September; 161(2):241-70.

van Corven E J, Groenink A, Jalink K, Eichholtz T, Moolenaar W H. Lysophosphatidate-induced cell proliferation: identification and dissection of signaling pathways mediated by G proteins. Cell. 1989 Oct. 6; 59(1):45-54.

Wang J, Carbone L D, Watsky M A. Receptor-mediated activation of a Cl(−) current by LPA and S1P in cultured corneal keratocytes. Invest Ophthalmol Vis Sci. 2002 October; 43(10):3202-8.

Watanabe N, Ikeda H, Nakamura K, Ohkawa R, Kume Y, Tomiya T, Tejima K, Nishikawa T, Arai M, Yanase M, Aoki J, Arai H, Omata M, Fujiwara K, Yatomi Y. Plasma lysophosphatidic acid level and serum autotaxin activity are increased in liver injury in rats in relation to its severity. Life Sci. 2007 Sep. 1; 81(12):1009-15.

Yamada T, Sato K, Komachi M, Malchinkhuu E, Tobo M, Kimura T, Kuwabara A, Yanagita Y, Ikeya T, Tanahashi Y, Ogawa T, Ohwada S, Morishita Y, Ohta H, Im D S, Tamoto K, Tomura H, Okajima F. Lysophosphatidic acid (LPA) in malignant ascites stimulates motility of human pancreatic cancer cells through LPA1. J Biol Chem. 2004 Feb. 20; 279(8):6595-605.

Yang M, Zhong W W, Srivastava N, Slavin A, Yang J, Hoey T, An S. G protein-coupled lysophosphatidic acid receptors stimulate proliferation of colon cancer cells through the {beta}-catenin pathway. Proc Natl Acad Sci USA. 2005 Apr. 26; 102(17):6027-32.

Yin Z, Tong Y, Zhu H, Watsky M A. ClC-3 is required for LPA-activated Cl− current activity and fibroblast-to-myofibroblast differentiation. Am J Physiol Cell Physiol. 2008 February; 294(2):C535-42.

The invention claimed is:
1. A compound of Formula (I):

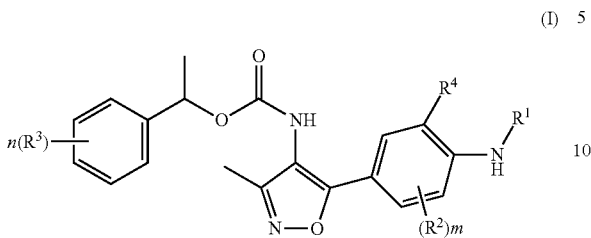

or a pharmaceutically acceptable salt, solvate, or prodrug thereof, wherein,
when $R^4$ is H, $R^1$ is C(=O)$R^5$ or SO$_2$$R^5$; or
$R^4$ and NHR$^1$, together with the two C atoms of the phenyl ring to which $R^4$ and NHR$^1$ are respectively attached, form a fused saturated, partially saturated or unsaturated 5-7 membered heterocycle which optionally contains 1-2 heteroatoms selected from N, O or S in addition to the N atom shown;
each $R^2$ and $R^3$ is independently selected from H, F, Cl, Br, CN, OH, or $C_1$-$C_4$alkyl;
$R^5$ is $C_1$-$C_6$ alkyl, $C_1$-$C_6$ aryl, $C_1$-$C_6$ alkoxyl, $C_{3-6}$ cycloalkyl, 5 or 6 membered heteroaryl containing 1-2 heteroatoms selected from N, O or S; 5-6 membered heterocyclyl containing 1-2 heteroatoms selected from N, O or S, wherein $C_1$-$C_6$ alkyl, $C_1$-$C_6$ aryl, $C_1$-$C_6$ alkoxyl, $C_{3-6}$ cycloalkyl, 5 or 6 membered heteroaryl and 5-6 membered heterocyclyl are optionally substituted with F, Cl, Br, I, —CN, —C(=O)—OH, —C(=O)—O—$C_{1-6}$ alkyl, —S(=O)$_2$—$C_{1-6}$ alkyl;
each m and n is 0, 1 or 2.

2. The compound according to claim 1 having Formula (II)

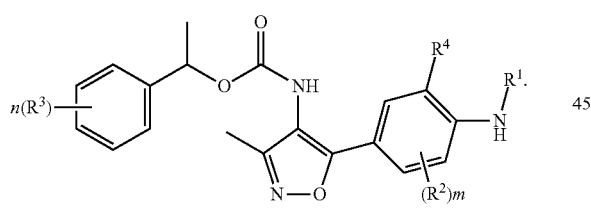

3. The compound according to claim 1, wherein an atom in any substituent group is H, $^2$H, $^3$H, $^{11}$C, $^{13}$C, $^{14}$C, $^{15}$N, $^{17}$O, $^{18}$O, $^{35}$S, $^{18}$F, $^{36}$I and/or $^{123}$I.

4. The compound according to claim 1, wherein the compound is selected from:
1-(2-chlorophenyl)ethyl(5-(1H-indol-5-yl)-3-methylisoxazol-4-yl)carbamate;
1-(2-chlorophenyl)ethyl(5-(1H-indazol-5-yl)-3-methylisoxazol-4-yl)carbamate;
1-(2-chlorophenyl)ethyl(5-(4-acetamidophenyl)-3-methylisoxazol-4-yl)carbamate;
1-(2-chlorophenyl)ethyl(3-methyl-5-(4-propionamidophenyl)isoxazol-4-yl)carbamate;
1-(2-chlorophenyl)ethyl(5-(4-isobutyramidophenyl)-3-methylisoxazol-4-yl)carbamate;
1-(2-chlorophenyl)ethyl(5-(4-(cyclopropanecarboxamido)phenyl)-3-methylisoxazol-4-yl)carbamate;
1-(2-chlorophenyl)ethyl(3-methyl-5-(methyl(4-methylisoxazol-3-yl)phenyl)carbamate)carbamate;
methyl 3-((4-(4-(((1-(2-chlorophenyl)ethoxy)carbonyl)amino)-3-methylisoxazol-5-yl)phenyl)amino)-3-oxopropanoate;
methyl 1-((4-(4-(((1-(2-chlorophenyl)ethoxy)carbonyl)amino)-3-methylisoxazol-5-yl)phenyl)carbamoyl)cyclopropanecarboxylate;
1-((4-(4-(((1-(2-chlorophenyl)ethoxy)carbonyl)amino)-3-methylisoxazol-5-yl)phenyl)carbamoyl)cyclopropanecarboxylic acid;
4-((4-(4-(((1-(2-chlorophenyl)ethoxy)carbonyl)amino)-3-methylisoxazol-5-yl)phenyl)amino)-4-oxobutanoic acid;
1-(2-chlorophenyl)ethyl(3-methyl-5-(4-(2-(methylsulfonyl)acetamido)phenyl)isoxazol-4-yl)carbamate;
1-(2-chlorophenyl)ethyl(5-(4-(2-cyanoacetamido)phenyl)-3-methylisoxazol-4-yl)carbamate;
1-(2-chlorophenyl)ethyl(5-(4-(2-ethoxyacetamido)phenyl)-3-methylisoxazol-4-yl)carbamate;
1-(2-chlorophenyl)ethyl(5-(4-benzamidophenyl)-3-methylisoxazol-4-yl)carbamate;
1-(2-chlorophenyl)ethyl(3-methyl-5-(4-(thiazole-2-carboxamido)phenyl)isoxazol-4-yl)carbamate;
4-((4-(4-(((1-(2-chlorophenyl)ethoxy)carbonyl)amino)-3-methylisoxazol-5-yl)phenyl)carbamoyl)benzoic acid;
(R)-1-(2-chlorophenyl)ethyl(3-methyl-5-(4-(methylsulfonamido)phenyl)isoxazol-4-yl)carbamate;
1-(2-chlorophenyl)ethyl(5-(4-(ethylsulfonamido)phenyl)-3-methylisoxazol-4-yl)carbamate;
1-(2-chlorophenyl)ethyl(3-methyl-5-(4-(1-methylethylsulfonamido)phenyl)isoxazol-4-yl)carbamate;
1-(2-chlorophenyl)ethyl(5-(4-(cyclopropanesulfonamido)phenyl)-3-methylisoxazol-4-yl)carbamate;
1-(2-chlorophenyl)ethyl(5-(4-(cyclohexanesulfonamido)phenyl)-3-methylisoxazol-4-yl)carbamate;
1-(2-chlorophenyl)ethyl(3-methyl-5-(4-(2,2,2-trifluoroethylsulfonamido)phenyl)isoxazol-4-yl)carbamate;
1-(2-chlorophenyl)ethyl(3-methyl-5-(4-(morpholine-4-sulfonamido)phenyl)isoxazol-4-yl)carbamate;
1-(2-chlorophenyl)ethyl(5-(4-(1-ethylpiperidine-4-sulfonamido)phenyl)-3-methylisoxazol-4-yl)carbamate;
methyl 3-(N-(4-(4-(((1-(2-chlorophenyl)ethoxy)carbonyl)amino)-3-methylisoxazol-5-yl)phenyl)sulfamoyl)propanoate;
3-(N-(4-(4-(((1-(2-chlorophenyl)ethoxy)carbonyl)amino)-3-methylisoxazol-5-yl)phenyl)sulfamoyl)propanoic acid;
1-(2-chlorophenyl)ethyl(3-methyl-5-(4-(phenylsulfonamido)phenyl)isoxazol-4-yl)carbamate;
1-(2-chlorophenyl)ethyl(3-methyl-5-(4-(pyridine-3-sulfonamido)phenyl)isoxazol-4-yl)carbamate;
1-(2-chlorophenyl)ethyl(5-(3-fluoro-4-(methylsulfonamido)phenyl)-3-methylisoxazol-4-yl)carbamate;
1-(2-chlorophenyl)ethyl(5-(2-fluoro-4-(methylsulfonamido)phenyl)-3-methylisoxazol-4-yl)carbamate;
1-(2-chlorophenyl)ethyl(5-(3,5-difluoro-4-(methylsulfonamido)phenyl)-3-methylisoxazol-4-yl)carbamate;
1-(2-chlorophenyl)ethyl(5-(3-chloro-4-(methylsulfonamido)phenyl)-3-methylisoxazol-4-yl)carbamate;
1-(2-chlorophenyl)ethyl(5-(2-chloro-4-(methylsulfonamido)phenyl)-3-methylisoxazol-4-yl)carbamate;
1-(2-chlorophenyl)ethyl(3-methyl-5-(3-methyl-4-(methylsulfonamido)phenyl)isoxazol-4-yl)carbamate;
1-(3-chlorophenyl)ethyl(3-methyl-5-(4-(methylsulfonamido)phenyl)isoxazol-4-yl)carbamate;

1-(3-fluorophenyl)ethyl(3-methyl-5-(4-(methylsulfonamido)phenyl)isoxazol-4-yl)carbamate;
1-(3,4-difluorophenyl)ethyl(3-methyl-5-(4-(methylsulfonamido)phenyl)isoxazol-4-yl)carbamate;
1-(3,4-dichlorophenyl)ethyl(3-methyl-5-(4-(methylsulfonamido)phenyl)isoxazol-4-yl)carbamate;
1-(4-chlorophenyl)ethyl(3-methyl-5-(4-(methylsulfonamido)phenyl)isoxazol-4-yl)carbamate;
1-(2-chloro-4-fluorophenyl)ethyl(3-methyl-5-(4-(methylsulfonamido)phenyl)isoxazol-4-yl)carbamate;
1-(2,4-dichlorophenyl)ethyl(3-methyl-5-(4-(methylsulfonamido)phenyl)isoxazol-4-yl)carbamate;
1-(4-chloro-2-fluorophenyl)ethyl(3-methyl-5-(4-(methylsulfonamido)phenyl)isoxazol-4-yl)carbamate;
(R)-1-(2-chloro-4-fluorophenyl)ethyl(3-methyl-5-(4-(methylsulfonamido)phenyl)isoxazol-4-yl)carbamate;
(R)-1-(2-chloro-4-fluorophenyl)ethyl(3-methyl-5-(4-(methylsulfonamido)phenyl)isoxazol-4-yl)carbamate;
(R)-1-(2-chlorophenyl)ethyl(5-(2-fluoro-4-(methylsulfonamido)phenyl)-3-methylisoxazol-4-yl)carbamate;
(R)-3-(N-(4-(4-(((1-(2-chlorophenyl)ethoxy)carbonyl)amino)-3-methylisoxazol-5-yl)phenyl)sulfamoyl)propanoic acid;
(R)-3-(N-(4-(4-(((1-(2-chlorophenyl)ethoxy)carbonyl)amino)-3-methylisoxazol-5-yl)-3-fluorophenyl)sulfamoyl)propanoic acid;
(R)-4-((4-(4-(((1-(2-chlorophenyl)ethoxy)carbonyl)amino)-3-methylisoxazol-5-yl)phenyl)amino)-4-oxobutanoic acid; or
(R)-4-((4-(4-(((1-(2-chlorophenyl)ethoxy)carbonyl)amino)-3-methylisoxazol-5-yl)-3-fluorophenyl)amino)-4-oxobutanoic acid.

5. A pharmaceutical composition comprising a therapeutically effective amount of a compound according to claim 1 or a pharmaceutically acceptable salt thereof and at least one pharmaceutically acceptable inactive ingredient.

6. The pharmaceutical composition according to claim 5, wherein the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

7. The pharmaceutical composition according to claim 6, wherein the pharmaceutical composition is a tablet or gelatin capsule comprising the present compound together with a) diluents, selected from lactose, dextrose, sucrose, mannitol, sorbitol, cellulose and/or glycine; b) lubricants, selected from silica, talcum, stearic acid, its magnesium or calcium salt and/or polyethyleneglycol; c) binders, selected from magnesium aluminum silicate, starch paste, gelatin, tragamayth, methylcellulose, sodium carboxymethylcellulose and/or polyvinylpyrrolidone; d) disintegrants, selected from starches, agar, alginic acid or its sodium salt, or effervescent mixtures; and/or e) absorbents, colorants, flavors and sweeteners.

8. The pharmaceutical composition according to claim 6, wherein the pharmaceutical composition is aqueous isotonic solution or suspension.

9. The pharmaceutical composition according to claim 6, wherein the pharmaceutical composition is a suppository and may be prepared from a fatty emulsion or a suspension.

* * * * *